US010717993B2

(12) United States Patent
Holmes et al.

(10) Patent No.: US 10,717,993 B2
(45) Date of Patent: Jul. 21, 2020

(54) METHODS AND COMPOSITIONS FOR INCREASED TRANSGENE EXPRESSION

(71) Applicant: Sangamo BioSciences, Inc., Richmond, CA (US)

(72) Inventors: Michael C. Holmes, Richmond, CA (US); Gary Ka Leong Lee, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 13 days.

(21) Appl. No.: 15/095,858

(22) Filed: Apr. 11, 2016

(65) Prior Publication Data

US 2016/0215298 A1   Jul. 28, 2016

Related U.S. Application Data

(63) Continuation of application No. 14/223,692, filed on Mar. 24, 2014, now abandoned, and a continuation-in-part of application No. 14/054,042, filed on Oct. 15, 2013, now Pat. No. 9,434,776, which is a continuation of application No. 13/068,348, filed on May 9, 2011, now Pat. No. 8,569,253, and a continuation of application No. 12/154,439, filed on May 22, 2008, now abandoned, and a continuation of application No. 11/805,707, filed on May 23, 2007, now Pat. No. 7,951,925.

(60) Provisional application No. 60/939,825, filed on May 23, 2007, provisional application No. 60/926,911, filed on Apr. 30, 2007, provisional application No. 60/847,269, filed on Sep. 26, 2006, provisional application No. 60/808,501, filed on May 25, 2006.

(51) Int. Cl.
| | |
|---|---|
| *C12N 15/861* | (2006.01) |
| *C12N 5/10* | (2006.01) |
| *C12N 15/52* | (2006.01) |
| *C12N 5/0783* | (2010.01) |
| *C12N 9/22* | (2006.01) |
| *C12N 15/86* | (2006.01) |
| *C12N 15/63* | (2006.01) |

(52) U.S. Cl.
CPC ........... *C12N 15/86* (2013.01); *C12N 5/0636* (2013.01); *C12N 15/63* (2013.01); *C12N 2501/2315* (2013.01); *C12N 2501/51* (2013.01); *C12N 2501/515* (2013.01); *C12N 2510/02* (2013.01); *C12N 2710/10343* (2013.01)

(58) Field of Classification Search
None
See application file for complete search history.

(56) References Cited

U.S. PATENT DOCUMENTS

| | | |
|---|---|---|
| 7,262,054 B2 | 8/2007 | Jamieson et al. |
| 7,273,923 B2 | 9/2007 | Jamieson et al. |
| 2003/0108880 A1 | 6/2003 | Rebar et al. |
| 2003/0232410 A1 | 12/2003 | Liljedahl et al. |
| 2005/0026157 A1 | 2/2005 | Baltimore |
| 2005/0026285 A1 | 2/2005 | Glimcher et al. |
| 2005/0064474 A1 | 3/2005 | Urnov et al. |
| 2005/0164387 A1 | 7/2005 | Flyer et al. |
| 2005/0208489 A1 | 9/2005 | Carroll |
| 2006/0188987 A1 | 8/2006 | Guschan et al. |
| 2006/0246567 A1 | 11/2006 | Rebar et al. |
| 2006/0246588 A1 | 11/2006 | Rebar et al. |
| 2007/0059795 A1 | 3/2007 | Moore et al. |
| 2007/0059833 A1 | 3/2007 | Li et al. |
| 2008/0159996 A1* | 7/2008 | Ando ................. C07K 14/4703 424/93.21 |
| 2008/0188000 A1 | 8/2008 | Reik et al. |

FOREIGN PATENT DOCUMENTS

| | | |
|---|---|---|
| EP | 1 939 278 A | 7/2008 |
| WO | WO 05/014791 A2 | 2/2005 |
| WO | WO 05/084190 A2 | 9/2005 |
| WO | WO 07/014275 A2 | 1/2007 |
| WO | WO 07/037780 A2 | 4/2007 |
| WO | WO 07/139898 A2 | 12/2007 |
| WO | WO 07/139982 A2 | 12/2007 |
| WO | WO 08/105887 A2 | 12/2008 |

OTHER PUBLICATIONS

Fukada et al, Functional Expression of the Chemokine Receptor CCR5 on Virus Epitope-Specific Memory and Effector CD8+ T Cells, J Immunol 2002; 168:2225-2232.*
Wilen, et al, Engineering HIV-Resistant Human CD4+ T Cells with CXCR4-Specific Zinc-Finger Nucleases, PLoS Pathog 7(4), 2011, pp. 1-15.*
Bai, et al., "Effective Transduction and Stable Transgene Expression in Human Blood Cells by a Third-Generation Lentiviral Vector," *Gene Therapy* 10(17):1446-1457 (2003).
Chen, et al., "High-Efficiency Gene Transfer to Primary T Lymphocytes by Recombinant Adenovirus Vectors," *J. Immunological Methods* 260:79-89 (2002).
Costello, et al., "Gene Transfer Into Simulated and Unsimulated T Lymphocytes by HIV-1-Derived Lentiviral Vectors," *Gene Therapy* 7(7):596-604 (2000).
Fecteau, et al., "CD40 Stimulation of Human Peripheral B Lymphocytes: Distinct Response From Naive and Memory Cells," *J. Immunology* 171(9):4621-4629 (2003).

(Continued)

*Primary Examiner* — Maria Marvich
(74) *Attorney, Agent, or Firm* — Pasternak Patent Law

(57) ABSTRACT

Described herein are methods of expressing nucleic acids in T cells pre-exposed to a co-stimulatory signal and then transduced with adenoviral vectors. In some embodiments, the co-stimulation is provided by anti-CD3 and anti-CD28 antibodies and the adenoviral vector is pseudotyped for T-cell entry. The invention also relates to compositions for carrying out these methods, provided as kits or pharmaceutical compositions that can be used to treat diseases including immunological conditions and hematological malignancies.

7 Claims, 11 Drawing Sheets

Specification includes a Sequence Listing.

(56) References Cited

OTHER PUBLICATIONS

Godfrey, et al., "In Vitro-Expanded Human CD4+CD25+ T-Regulatory Cells Can Markedly Inhibit Allogeneic Dendritic Cell-Stimulated MLR Cultures," *Blood* 104(2):453-461 (2004).

Gordley, et al., "Evolution of Programmable Zinc Finger—Recombinases with Activity in Human Cells," *Journal of Molecular Biology* 367:802-813 (2007).

Kalady, et al., "Enhanced Dendritic Cell Antigen Presentation in RNA-Based Immunotherapy," *Journal of Surgical Research* 105(1):17-24 (2002).

Kalady, et al., "Enhanced Dendritic Cell Antigen Presentation in RNA-Based Immunotheraphy," *Journal of Surgical Research* 105(1):17-24 (2002).

Kruisbeek, et al., "Proliferative Assays for T Cell Function," *Current Protocols in Immunology* 3.12.1-3.12.20 (2004).

Leen, et al., "T-Cell Immunotheraphy for Adenoviral Infections of Stem-Cell Transplant Recipients," *Ann. N.Y. Acad. Sci* 1062:104-115 (2005).

Lu, et al., "Safe Two-Plasmid Production for the First Clinical Lentivirus Vector That Achieves >99% Transduction in Primary Cells Using a One-Step Protocol," *J. Gene Medicine* 6(9):963-973 (2004).

Mercier, et al., "Adenovirus Fibre Exchange Alters Cell Tropismin Vitro but not Transgene-Specific T CB8+ Immune Responses in Vivo," *J. General Virology* 85:1227-1236 (2004).

Pollok, et al., "High-Efficiency Gene Transfer Into Normal and Adenosine Deaminase-Deficient T Lymphocytes is Mediated by Transduction on Recombinant Fibronectin Fragments," *J. Virology* 72(6):4882-4892 (1998).

Reik, et al., "Designer Cells for Cellular Immunotherapy: Zinc Finger Nuclease (ZFN) Stimulated Targeted Recombination for the Simultaneous Disruption of the Endogenous Glucocorticoid Receptor and Site-Specific Addition of the IL 13-Zetakine," *Blood* 108:Abstract 3705 (2006).

Sangamo News Release, "Sangamo Biosciences Announces Positive HIV/CCR5-ZFN Data in Presentation at 46th Annual Interscience Conference on Antimicrobial Agents and Chemotherapy," Sep. 27, 2006.

Schroers, et al., "Gene Transfer Into Human T Lymphocytes and Natural Killer Cells by Ad5/F35 Chimeric Adenoviral Vectors," *Experimental Hematology* 32(6):53646 (2004).

Tatsis et al., "Adenoviral Vectors Persist in Vivo and Maintain Activated CD8+ T Cells: Implications for Their Use as Vaccines," *Blood* 110:1916-1923 (2007), Prepublished online May 17, 2007.

Trickett, et al., "T Cell Stimulation and Expansion Using Anti-CD3/CD28 Beads," *Journal of Immunological Methods* 275:251-255 (2003).

Tripathi, et al., "An Adenoviral Vector for Probing Promoter Activity in Primary Immune Cells," *J. Immunol, Methods*. 311(1-2):19-30 (2006) doi:10.1016/j.jim.2006.01.009.

Unutmaz, et al., "Cytokine Signals are Sufficient for HIV-1 Infections of Resting Human T Lymphocytes," *J. Exp. Med.* 189(11):1735-1746 (1999).

Voss, et al., "Participation of the CD94 Receptor Complex in Costimulation of Human Natural Killer Cells," *J. Immunology*. 160(4):1618-1626 (1998).

Wen, et al., "4-1BB Ligand-Mediated Costimmulation of Human T Cells Induces CD4 and CD8 T Cell Expansion, Cytokine Production and the Development of Cytolytic Effector Function," *J. Immunology* 168(10):4897-4906 (2002).

Yamashita, et al., "Retroviral Infection of Non-Dividing Cells: Old and New Perspectives," *Virology* 344(1):88-93 (2006).

Yotnda, et al., "Targeted Delivery of Adenoviral Vectors by Cytotoxic T Cells," *Blood* 104(8):2272-2280 (2004).

\* cited by examiner

METHODS AND COMPOSITIONS FOR INCREASED TRANSGENE EXPRESSION

CROSS-REFERENCE TO RELATED APPLICATIONS

The present application is a continuation of U.S. patent application Ser. No. 14/223,692, filed Mar. 24, 2014, now abandoned, which is a continuation of U.S. application Ser. No. 12/154,439, filed May 22, 2008, now abandoned, which in turn claims the benefit of U.S. Provisional Application No. 60/939,825, filed May 23, 2007. The present application is also a continuation-in-part of U.S. application Ser. No. 14/054,042, filed Oct. 15, 2013, now issued as U.S. Pat. No. 9,434,776, which is a continuation of U.S. patent application Ser. No. 13/068,348, filed May 9, 2011, issued as U.S. Pat. No. 8,569,253, which is a continuation of U.S. patent application Ser. No. 11/805,707, filed May 23, 2007, issued as U.S. Pat. No. 7,951,925, which claims the benefit of U.S. Provisional Application No. 60/808,501, filed May 25, 2006; U.S. Provisional Application No. 60/847,269, filed Sep. 26, 2006 and U.S. Provisional Application No. 60/926,911, filed Apr. 30, 2007. The disclosures of all the foregoing are incorporated by reference in their entireties for all purposes.

STATEMENT OF RIGHTS TO INVENTIONS MADE UNDER FEDERALLY SPONSORED RESEARCH

Not applicable.

TECHNICAL FIELD

The present invention relates generally to improved methods and compositions for expressing exogenous nucleic acids in cells, and more particularly to improved expression of exogenous genetic material in human immune cells using adenoviral vectors.

BACKGROUND

Reliable transgene expression in immune effector cells such as T cells can provide needed insight into immunological mechanisms, and would also help enable novel immunotherapeutic strategies such as, e.g., gene therapy approaches for treating cancer as well as immunological, hematological, infectious, and genetic disorders. Unfortunately, however, stable and effective transgene expression in T cells has proven to bean elusive goal, often requiring hit-or-miss experimentation. It is well-established, for example, that transduction of resting primary T lymphocytes with viral vectors, such as retroviral derived vectors, generally results in very low efficiencies [Yamashita and Emerman, J. Virology 2006 Jan. 5; 344(1):88-93]. Accordingly, studies in retroviral-mediated gene transfer to primary T lymphocytes over the past ten years have examined a number of different strategies to improve transduction efficiencies, leaving the even greater hurdle of satisfactory transgene expression as a more distant goal.

With respect to viral systems providing permanent integration into the host cell, it has been shown that T cell activation in conjunction with lentiviral transduction can significantly improve gene delivery to T cells. See, e.g., Unutmaz et al., J Exp Med. 1999 Jun. 7; 189(11):1735-46; Pollock et al., J. Virology, 1998 June; 72(6):4882-92; Costello et al., Gene Ther. 2000 April; 7(7):596-604; Bai et al., Gene Ther. 2003 August; 10(17):1446-57; Lu et al., J Gene Med. 2004 September; 6(9):963-73. Bai et. al. and Lu et. al., for example, independently reported that both phytohemagluttinin (PHA) and anti-CD3/antiCD28 costimulation of T lymphocytes can improve lentiviral gene delivery efficiencies, demonstrating 80 to >99% transduction. Despite these reported successes in transduction efficiency, however, the actual levels of gene expression obtained by these researchers is inconclusive based on the reported data.

Unfortunately, however, attempts to reproduce these results using non-integrative viral systems have been more problematic. See, e.g., Schroers et al., Exp Hematol. 2004 June; 32(6):53646. In the Schroers study, PHA activation provided only a modest improvement in transduction efficiency with adenoviral vectors, approaching only 45 percent transduction, significantly lower than that obtained using lentiviral vectors. Thus, there remains a significant need in the art for improved methods and compositions capable of high transgene expression in T cells in non-integrative viral systems, e.g., to provide proteins of therapeutic, industrial, or research uses. The present invention addresses this and other needs.

SUMMARY

The present invention derives from the surprising finding that a T cell co-stimulatory signal, unlike other forms of T cell activation, significantly improves adenoviral-mediated transduction of T cells with exogenous nucleic acids and, more importantly, produces high expression levels of an encoded exogenous molecule. The compositions and methods described herein allow for increased transient expression of any exogenous sequence in any T cell. Accordingly, the need for an integrating vector (retrovirus or lentivirus), which vectors can cause insertional mutagenesis or variegated expression due to position effects, is eliminated. In addition, the ability to transiently express exogenous sequences in T cells may provide for more stable cell populations, for example in that immunogenic peptides may be cleared out before the host immune system can mount a response. Thus, as described herein, the exogenous molecule may be any diagnostic or a therapeutic molecule of interest, thus providing novel methods of diagnosing, treating and/or preventing a wide variety of conditions and disorders.

In one aspect, methods for increasing expression of an exogenous nucleic acid in T cells are provided, comprising 1) activating a population of T cells in vitro or ex vivo with a co-stimulatory signal produced by at least a first and second co-stimulatory agent; and 2) contacting said activated T cell population with an adenoviral expression vector comprising said exogenous nucleic acid; wherein said contacting results in expression of a transgene encoded by the exogenous nucleic acid in greater than 50% of said activated T cells. In one embodiment, the T cell is a CD4+ T cell. In another embodiment, the T cell is a CD8+ T cell.

In a preferred embodiment, the co-stimulatory signal includes activation of the T cell receptor, and employs a co-stimulatory agent comprising a CD3 ligand. In a particularly preferred embodiment, the CD3 ligand comprises an anti-CD3 antibody. In certain embodiments, expression of the endogenous gene is at least about three fold greater, preferably at least about five fold greater and even more preferably at least about six fold greater as compared to T cell activated with PHA and/or IL 2 and transduced with an adenoviral vector.

In a preferred embodiment, the co-stimulatory signal also includes activation of the CD28 receptor, and the co-stimulatory agent further comprises a CD28 ligand. In a particularly preferred embodiment the CD28 ligand comprises a CD28 antibody.

In an alternative embodiment, the co-stimulatory agent further comprises IL-15. In another alternative embodiment, the co-stimulatory signal further comprises a feeder cell.

In a preferred embodiment, the adenoviral expression vector is pseudotyped to enhance targeting of immune cells, e.g., T cells. In one embodiment, the pseudotyped adenovirus expression vector comprises sequences from Ad5 and Ad35 adenoviruses. In a particular embodiment, the Ad35 sequence is F35. In another embodiment, the pseudotyped adenovirus expression vector comprises sequences from Ad5 and Ad 11 adenoviruses.

In one aspect, the exogenous nucleic acid encodes a diagnostic molecule such as, e.g. a fluorescent protein (e.g., GFP or RFP).

In another aspect, the exogenous nucleic acid encodes a therapeutic molecule such as, e.g., an RNA molecule or a therapeutic protein. In preferred embodiments, the therapeutic protein is selected from the group consisting of hormones, enzymes, cytokines, chemokines, antibodies, mitogenic factors, growth factors, differentiation factors, factors influencing angiogenesis, factors influencing cell apoptosis, and factors influencing inflammation.

In another aspect, the exogenous nucleic acid encodes for a molecule capable of disrupting, enhancing or altering endogenous gene expression such as, e.g., transcription factors or nucleases. In preferred embodiments, the exogenous nucleic acid encodes for a zinc finger protein. In a particular embodiment, the zinc finger protein is directed to CCR5.

In another aspect, the exogenous nucleic acid sequence may produce one or more non-coding sequences, for example, one or more RNA molecules (e.g., small hairpin RNAs (shRNAs), small interfering RNAs (siRNAs), inhibitory RNAs (RNAis), microRNAs (miRNAs), etc.).

In one aspect, the invention provides an improved method of integrating an exogenous sequence into a T cell, said method comprising: a) activating said T cell with a co-stimulatory signal; and exposing said activated T cell to an adenoviral vector comprising said exogenous sequence, for example, using ZFN-mediated targeted integration. In certain embodiments, the integration of the exogenous sequence is at least about 70% to 90% efficient, including any value therebetween (e.g., 70%, 71%, 72%, 73%, 74%, 75%, 76%, 77%, 78%, 79%, 80%, 81%, 82%, 83%, 84%, 85%, 86%, 87%, 88%, 89%, 90%).

In one aspect, kits for expressing and/or integrating an exogenous sequence in T cells are provided comprising a costimulatory agent as described herein and an adenoviral expression vector.

In one aspect, methods of cleaving an endogenous gene in a cell are provided comprising expressing at least one zinc finger nuclease in a T cell according to any of the methods described herein, such that the zinc finger nuclease(s) cleave(s) the endogenous gene. In certain embodiments, the zinc finger nuclease cleaves a gene encoding a receptor involved in HIV entry into a cell (e.g., CCR5). In other embodiments, the zinc finger nuclease(s) cleave(s) a glucocorticoid receptor (GR). Thus, also provided are methods of preventing and/or treating HIV by expressing a CCR-5 binding zinc finger nuclease in a T cell. Methods of retaining T cell immune function during glucocorticoid treatment by cleaving a GR are also provided.

Additional features and advantages of the invention will be set forth in the detailed description which follows, and in part will be readily apparent to those skilled in the art from that description or recognized by practicing the invention as described herein, including the detailed description which follows, the claims, as well as the appended figures.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The figures illustrate various embodiments of the invention, and together with the description serve to explain the principles and operations of the invention.

DETAILED DESCRIPTION

Figure 1:
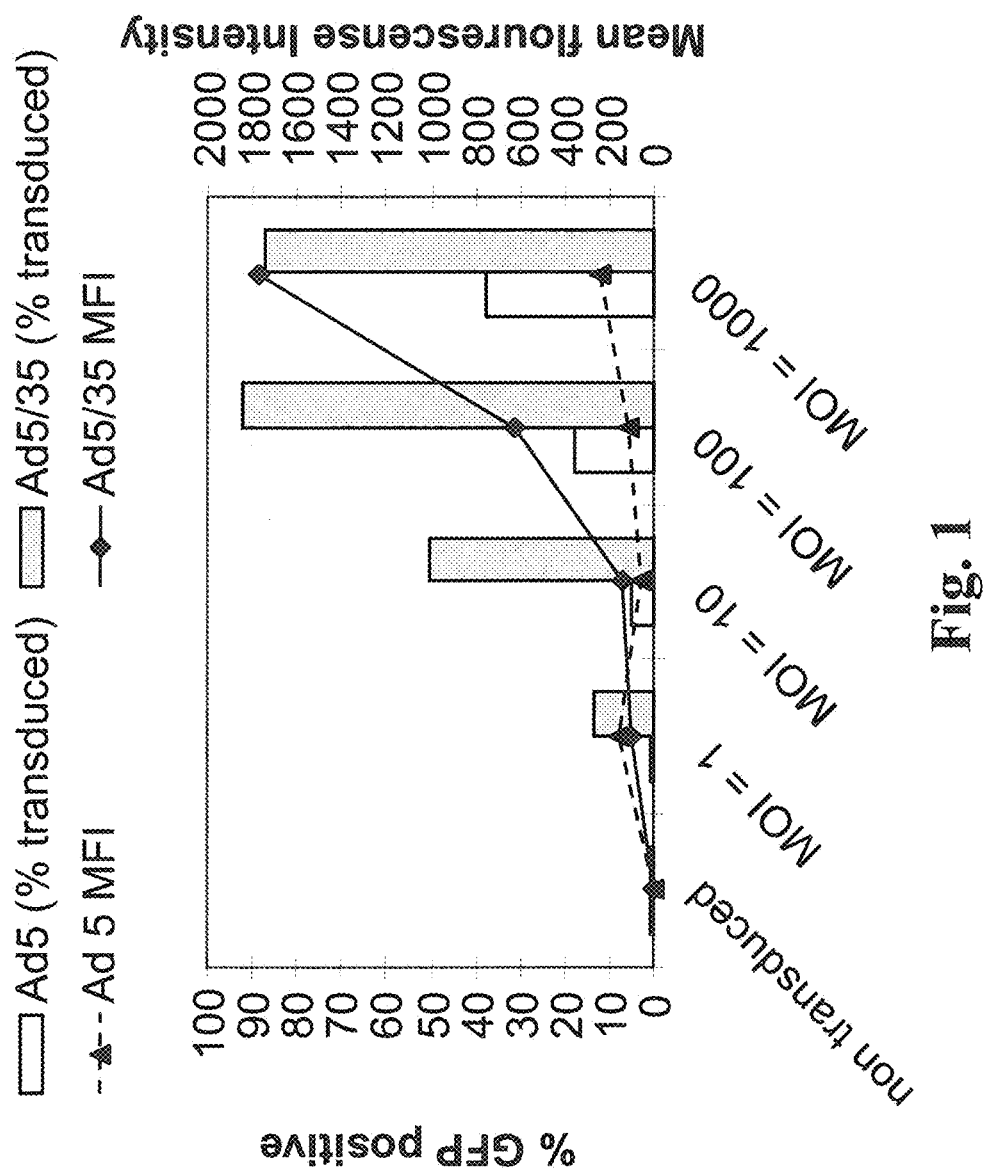
FIG. 1 illustrates transduction and expression of GFP in primary T lymphocytes using either Ad5 or Ad5/F35 GFP adenoviral vectors, following activation with anti-CD3/anti-CD28 antibodies.

Reference will now be made in detail to the present preferred embodiments of the invention, examples of which are illustrated in the accompanying figures.

The present invention relates to methods and compositions for transducing exogenous nucleic acids into T cells using non-integrative viral vectors such as, e.g., adenoviral vectors, and particularly to the expression of transgenes contained therein. The invention is at least partly based on the surprising results obtained with respect to high transgene expression as well as transduction efficiency in T cells when activated with a co-stimulatory signal and transduced with adenoviral vectors carrying the exogenous genetic material.

One aspect of the present invention relates to methods for expressing exogenous nucleic acids in T cells. In preferred embodiments, the invention provides improved methods for introducing exogenous nucleic acids encoding a transgene into a cell, where the transgene is expressed. An "exogenous nucleic acid" can be defined as any nucleic acid introduced into a cell. The exogenous nucleic acid may encode a polypeptide product. Alternatively, the exogenous nucleic acid sequence may produce one or more non-coding sequences, for example, one or more RNA molecules (e.g., small interfering RNAs (siRNAs), small hairpin RNAs (shRNAs), inhibitory RNAs (RNAis), microRNAs (miRNAs), etc.). The exogenous nucleic acid may or may not correspond to a sequence (e.g., gene) otherwise found or expressed in the cell. For example, the "exogenous" nucleic acid may correspond to a gene normally found in healthy T cells, but not found or found to a lesser extent, or expressed to a lesser extent, in the T cells being transduced. "Transgene" as used herein refers to an exogenous gene that is introduced into cells to be expressed, i.e., transcribed and/or translated into a polypeptide product. "Exogenous nucleic acid" is also used interchangeably herein with "exogenous genetic material."

The term "nucleic acid" as used herein can refer to a deoxyribonucleotide or ribonucleotide polymer in either single- or double-stranded form. The term is used to indicate, for example, genes, cDNAs, and mRNAs. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. The term also encompasses nucleic acids containing modified backbone residues or linkages, which are synthetic, naturally occurring, and non-naturally occurring. Examples of such analogs include, without limitation, phosphorothioates, phosphoramidates, methyl phosphonates, chiral-methyl phosphonates, 2-0-methyl ribonucleotides, peptide-nucleic acids (PNAs).

The T cells transduced by the methods of the present invention can be any T cell of any mammalian animal. As used herein, "T cell" is used interchangeably with "T lymphocyte." In preferred embodiments, the T cell is a primary T lymphocyte, more preferably a human primary T lymphocyte. In some preferred embodiments, the T cell is a CD4+ cell. The T cell can also be a CD8+ cell, or a mixture of CD4+ and CD8+ cells. T cells for use in the subject compositions and methods can be obtained and/or accessed by methods well known in the art. Samples can be used immediately or frozen for future use. Frozen samples can be thawed and cultured in appropriate media before use, according to methods known in the art.

Co-Stimulatory Signals

The methods of the present invention involve activating the T cells with a co-stimulatory signal. A "co-stimulatory signal" as used herein refers to a coordinated activation signal employing at least two co-stimulatory agents. In preferred embodiments, the co-stimulatory signal includes activation of the T cell receptor, and the first co-stimulatory agent comprises a CD3 ligand, and preferably an anti-CD3 antibody. In preferred embodiments for T cells, and CD4+ T cells in particular, the co-stimulatory signal further includes activation of the CD28 receptor, and the second costimulatory agent comprises a CD28 ligand, and preferably an anti-CD28 antibody. In alternative embodiments for CD8+ T cells, the co-stimulatory signal further includes activation of the IL-15 receptor, and the second co-stimulatory agent comprises IL-15. In some embodiments, the antibodies are provided on beads such as, e.g., Dynalbead CD3/CD28 (Invitrogen, Carlsbad, Calif.).

While co-stimulation of the CD3 and CD28 pathways are required for optimal transduction of CD4+ T cells, as shown herein, additional hematopoietic cell lineages also require co-stimulation through at least two distinct pathways (e.g. a mitogen signal and a signal associated with cell-cell contact) to achieve complete activation. Accordingly, the methods described herein may be applicable to other cell types, using similar adenoviral vectors but co-stimulatory signals appropriate for the particular cell type. Examples include, but are not limited to, CD8+ T cells co-stimulated by anti-CD3 and CD 137ligand (4-1BBL) [Wen et al., J Immunol. 2002 May 15; 168(10):4897-906).], B lymphocytes co-stimulated by CD40L and IL4 [Fecteau et al.; J Immunol. 2003 Nov. 1; 171(9):4621-9], and subsets of NK cells being co-stimulated by anti-CD94 antibodies and IL2 or IL15 [Voss et at., J. Immunol. 1998 Feb. 15; 160(4)1618-26].

Expression Vectors

A further step of the present methods involves exposing the activated cells to a vector carrying exogenous genetic material to be expressed. The term "vector" as used herein refers to a carrier nucleic acid molecule into which a nucleic acid sequence can be inserted for introduction into a cell where, in some embodiments, it can be replicated. In preferred embodiments, the vector is an expression vector. By "expression vector" is meant a vector containing the appropriate control sequences to permit transcription and, optionally, translation of an exogenous gene in a transduced cell. Typically, the expression vector includes an "expression cassette," which comprises a nucleic acid to be transcribed operably linked to a promoter. For example, the expression vector may contain a promoter sequence in the regulatory region which facilitates the transcription of (and is operably linked to) an inserted nucleic acid sequence. An expression vector also includes a vector that directs transcription of a sequence, for example, one or more RNA molecules (e.g., small hairpin RNAs (shRNAs), small interfering RNAs (siRNAs), inhibitory RNAs (RNAis), microRNAs (miRNAs), etc.)

In more preferred embodiments, the vector is an adenoviral expression vector. Adenoviruses contain a linear double-stranded DNA molecule of approximately 36,000 base pairs with identical inverted terminal repeats ("ITRs")

of approximately 90-140 base pairs. The exact length of the ITRs depends on the adenovirus serotype. Adenoviruses have been used as vectors to achieve transduction and transgene expression in various cell types by capitalizing on their mechanisms of infection. For example, using Ad5 vectors, the initial step for successful infection is binding of adenovirus to its target cell, a process mediated through their fiber proteins. The fiber protein has a trimeric structure (Stouten, P. W. F., Sander, C., Ruigrok, R. W. H., and Cusack, S. (1992) New triple helical model for the shaft of the adenovirus fiber. J. Mol. Biol. 226, 1073-1084) with different lengths depending on the virus serotype (Signas, G., Akusjarvi, G., and Petterson, U. (1985). Adenovirus 3 fiberpolypeptide gene: Complications for the structure of the fiber protein. Journal of Virology. 53, 672-678; Kidd, A. H., Chrboczek, J., Cusack, S., and Ruigrok, R. W./H. (1993) Adenovirus type 40 virions contain two distinct fibers. Virology 192, 73-84). Different serotypes have polypeptides with structurally similar N and C termini, but different middle stem regions. The first 30 amino acids at the N terminus are involved in anchoring of the fiber to the penton base (Chroboczek J., Ruigrok R. W. H., and Cusack S., 1995. Adenovirus fiber, p. 163-200. In: W. Doerfer and P. Bohm (ed.), The molecular repertoire of adenoviruses, I. Springer-Verlag, Berlin), especially the conserved FNPVYP region in the tail (Amberg N., Mei Y. and Wadell G., 1997. Fiber genes of adenoviruses with tropism for the eye and the genital tract. Virology 227: 239-244). The C-terminus, or "knob", is responsible for initial interaction with the cellular adenovirus receptor. After this initial binding, secondary binding between the capsid penton base and cell-surface integrins leads to internalization of viral particles in coated pits and endocytosis (Morgan, C., Rozenkrantz, H. S., and Mednis, B. (1969) Structure and development of viruses as observed in the electron microscope.X. Entry and uncoating of adenovirus. J. Virol 4, 777-796; Svensson, V. and Persson, R. (1984). Entry of adenovirus 2 into Hela cells. Journal of Virology. 51, 687-694; Varga, M. J., Weibull, C., and Everitt, E. (1991). Infectious entry pathway of adenovirus type 2. Journal of Virology 65, 6061-6070; Greber, U. F., Willets, M., Webster, P., and Helenius, A. (1993). Stepwise dismanteling of adenovirus 2 during entry into cells. Cell 75, 477-486; Wickham, T. J., Mathias, P., Cherish, D. A., and Nemerow, G. R. (1993) Integrins avb3 and avb5 promote adenovirus internalisation but not virus attachment. Cell 73, 309-319). Integrins are αβ-heterodimers of which at least 14 α-subunits and 8 β-subunits have been identified (Hynes, R. 0. (1992) Integrins: versatility, modulation and signaling in cell adhesion. Cell 69, 11-25). The array of integrins expressed in cells is complex and will vary between cell types and cellular environment. Although the knob contains some conserved regions, between serotypes, knob proteins show a high degree of variability, indicating that different adenovirus receptors exist.

Some other adenoviral vectors may use other mechanisms for entry. For example, subgroup B adenoviruses, such as Ad35, utilize human CD46 as a cellular attachment receptor (Gaggar et. al. (2003) Nature Medicine, Vol 9, pp. 1408-1412). It has also been demonstrated that chimeric Ad5135 vectors possess the same receptor specificity as Ad35, thus allowing for CAR-independent transduction of cells, such as human hematopoetic cells (Nilsson et. al., (2004), Molecular Therapy, Vol. 9, pp. 377-388).

At least six different subgroups of human adenoviruses have been proposed, encompassing approximately 50 distinct adenovirus serotypes. Besides these human adenoviruses, many animal adenoviruses have been identified (see, e.g., Ishibashi, M. and Yasue (1983) in Adenoviruses of Animals, Chapter 12, p 497-561). A serotype can be defined on the basis of its immunological distinctiveness as determined by quantitative neutralization with animal antiserum (horse, rabbit). If neutralization shows a certain degree of cross-reaction between two viruses, distinctiveness of serotype is assumed if A) the hemagglutinins are unrelated, e.g., as shown by lack of cross-reaction on hemagglutination-inhibition, or B) substantial biophysical/biochemical differences in DNA exist (Francki, R. I. B., Fauquet, C. M., Knudson, D. L. and Brown, F. (1991) Classification and nomenclature of viruses. Fifth report of the international Committee on taxonomy of viruses. Arch. Virol. Suppl. 2, 140-144). Besides differences towards the sensitivity against neutralizing antibodies of different adenovirus serotypes, adenoviruses in subgroup C such as Ad2 and Ad5 bind to different receptors as compared to adenoviruses from subgroup B such as Ad3, Ad7, Ad11, Ad14, Ad21, Ad34, and Ad35 (see, e.g., Defer C., Belin M., Caillet-Boudin M. and Boulanger P., 1990. Human adenovirus-host cell interactions; comparative study with members of subgroup B and C. Journal of Virology 64 (8): 3661-3673; Gall J., Kass-Eisler A., Leinwand L. and Falck-Pedersen E., 1996. Adenovirus type 5 and 7 capsid chimera: fiber replacement alters receptor tropism without affecting primary immune neutralization epitopes. Journal of Virology 70 (4): 2116-2123).

Pseudotyping of adenoviral vectors can be made possible primarily by swapping the knob region of the fiber protein of one adenovirus serotype with that of another serotype [Stevenson, J Virol. 1997 June; 71(6):4782-90]. This type of fiber protein manipulation allows for modification of the vector tropism, i.e., allows for transduction of a different range of cell types [Mizuguchi 2002 (Adenovirus vectors containing chimeric type 5 and type 35 fiber proteins exhibit altered and expanded tropism and increase the size limit of foreign genes. February 20; 285(1-2):69-77., Takayama et al., Virology. 2003 May 10; 309(2):282-93.); Stecher et al. Mol Ther. 2001 July; 4(1):36-44]. Construction of such chimeric adenoviral vectors is known in the art. For example, it has been demonstrated that receptor specificity could be altered by exchanging the Ad3 knob protein with the Ad5 knob protein, and vice versa (Krasnykh V. N., Mikheeva G. V., Douglas J. T. and Curiel D. T., 1996. Generation of recombinant adenovirus vectors with modified fibers for altering viral tropism. Journal of Virology 70(10): 6839-6846; Stevenson S. C., Rollence M., White B., Weaver L. and McClelland A., 1995. Human adenovirus serotypes 3 and 5 bind to two different cellular receptors via the fiber head domain. Journal of Virology 69(5): 2850-2857 Stevenson S. C., Rollence M., Marshall-Neff J. and McClelland A., 1997. Selective targeting of human cells by a chimeric adenovirus vector containing a modified fiber protein. Journal of Virology 71(6): 4782-4790; see also, e.g., Yotnda et al., Gene Ther. 2001 June; 8(12):930-7).

In some embodiments, the adenovirus expression vector is pseudotyped. For example, the vector can comprise a chimeric adenoviral vector, that is, a genetically modified vector comprising nucleic acid sequences from two or more adenoviruses (plus an exogenous gene). Typically, the nucleic acid sequences will correspond to adenoviral proteins from adenoviruses of two different serotypes. In preferred embodiments, the vector comprises a sequence corresponding to at least one tissue tropism determining fragment of a fiber protein derived from a subgroup B adenovirus, where the tropism is directed towards T-cells. In more preferred embodiments, the vector comprises sequences from Ad5 and Ad35 adenoviruses, for example, where the Ad5 fiber genes are substituted by the Ad35 fiber genes. In still more preferred embodiments, the Ad35 sequences corresponding to the Ad35 gene encode the knob portion of the fiber protein, known as F35. Such a vector can be referred to as an Ad5/F35 vector. In some embodiments, the vector comprises Ad5 and Ad11 sequences. In still some other embodiments, a combination of adenoviral vectors can be used, e.g., a combination of any of the kinds of adenoviral expression vectors and/or chimeric adenoviral vectors described herein.

Those of skill in the art will recognize other modifications or alterations that can be made to the adenoviral vector in the practice of some embodiments of the instant invention. For example, in some embodiments, the adenoviral vector is modified such that the capacity of the adenoviral nucleic acid to replicate in a target cell is reduced or disabled. In some embodiments, the adenoviral nucleic acid is modified so that the capacity of a host immune system to mount an immune response against adenoviral proteins encoded by the adenovirus nucleic acid is reduced or disabled. In some embodiments, the adenoviral nucleic acid is modified so as to be integrative into the host cell genome. For example, in some embodiments homologous sequences are used to integrate at least a portion of adenoviral nucleic acid into the host cell's genome, e.g., via targeted homologous recombination.

According to methods of the instant invention, the vector is allowed to transduce the T-cell, e.g., by exposing the T-cells to the vector under conditions suitable for transduction. For example, T lymphocyte cultures can be incubated at about 37° C., 5% $CO_2$. A vector can be said to "transduce" a cell where the vector enters the cell. Entry may be by any process, e.g., receptor-mediated endocytosis, by which particles are taken up by cell. As outlined in more detail above, uptake of some adenovirus particles is generally a two-stage process involving an initial interaction of the fiber protein of the virus with cellular receptors, such as the MHC class I molecule and the coxsackievirus-adenovirus receptor. Viral penton proteins then bind to integrin cell receptors, facilitating internalization via receptor-mediated endocytosis. For example, this is the mechanism used by A5 vectors. Other adenoviral vectors, e.g., AD5/35 vectors, utilize CD46 for entry. Adenovirus vectors can be readily constructed using methods known in the art and/or commercially available kits such as the AdEasy™ Kits (Strategene, La Jolla, Calif.).

In still some embodiments of the instant invention, one or more of the adenoviral vectors described herein are used in combination with other approaches known in the art. For example, a mixture of adenoviral and lentiviral vectors may be used to achieve transduction.

As known to those in the art, vectors can be added directly to the T cells at various dilutions to achieve varying MOIs (multiplicities of infection). For example, vectors can be diluted with culture medium an MOI in the range of about 10 to about 1000 infectious units per cell. One advantage obtained from use of the present invention is that the MOI can be reduced to levels that are less toxic to human immune cells and T cells in particular, while still achieving efficient adenovirus transduction and an adequate level of transgene expression.

In some preferred embodiments, a CD4+ cell is activated using beads coated with anti-CD3 and anti-CD28 antibodies and transduced with Ad5/F35 vectors carrying the exogenous gene to be introduced.

Following transduction, the exogenous gene can then be expressed in the T cells. As described in greater detail in the Examples below, some embodiments of the instant invention provided surprisingly and unexpectedly higher transgene expression levels compared to that obtained using methods described previously (e.g., using lentiviral gene delivery). Moreover, methods of some embodiments of the instant invention produce at least about 3-fold, at least about 5-fold, at least about 10-fold, at least about 15-fold or at least about 20-fold improvement over using no T cell activation.

For example, in preferred embodiments, the methods provided herein result in increased levels of expression of the exogenous gene as compared with methods previously described in the art. For example, methods herein can provide at least about 2-fold, at least about 3-fold, or at least about 4-fold the level of expression obtained using no co-stimulatory signal. Moreover, the present invention can also provide improved levels of expression compared with known methods for activating the cells. For example, compared to pre-stimulation with PHA or IL 2, methods of some embodiments of the instant invention provide at least about 3-fold, at least about 4-fold, at least about 5-fold or at least about 6-fold the level of transgene expression See, e.g., Examples provided below where transgene expression levels are measured via mean fluorescent intensity of GFP, using a GFP gene as the transgene.

In some embodiments, methods of the instant invention provide at least about 3-fold, at least abut 5-fold, at least about 10-fold or even at least about 15-fold the level of transgene expression when compared to pre-stimulation with PHA or IL2. See, e.g., Examples provided below where transgene expression levels are measured via the rate of NHEJ events caused by expression of a nuclease encoded as the transgene. Also see FIG. 11, that illustrates the difference in CCR5 gene modification in CD4+ T cells exposed to Ad5/F35 vectors carrying a zinc finger nuclease directed to CCR5 when pre-stimulated with either PHA or anti-CD3/anti-CD28 antibodies.

Transduction can result in either transient or stable expression. Where the transgene becomes stably integrated into a host's genome, for example, stable expression can be obtained. In some applications, transient expression is more preferred. For example, one approach involves using almost homologous sequences that differ from a region on the host's genome by one nucleotide. Integration in such cases can occur at high frequencies, e.g., 1 in 10 or 1 in 20, but as cells divide, the nucleotide difference is corrected. This approach can achieve high transduction efficiencies and high but transient transgene expression.

One of skill in the art will also recognize applications where the exogenous nucleic acid introduced into a cell need not be expressed. For example, methods of some embodiments of the present invention can deliver nucleic acid sequences that are useful in themselves. Nucleic acid sequences that are transcribed but not translated include, for example, aptamers, ribosomal RNA, tRNA, splicosomal RNA, antisense RNA, siRNA, shRNA, miRNA and mRNA. Accordingly, another aspect of the instant invention relates to methods for transducing T-cells by activating the T-cell with a costimulatory signal, exposing it to an adenoviral vector carrying the exogenous gene and allowing the vector to enter the T-cell. The cells, vectors and co-stimulatory signals described above can also be used with respect to this aspect of the invention. Preferred embodiments of the instant invention provide for increased transduction efficiencies with respect to introducing exogenous genetic material into T cells. For example, in some embodiments, transduction is at least about 60%, at least abut 65%, at least about 70% or, at least about 80%, efficient. Nucleic acid delivery efficiencies can be measured by various techniques known in the art. Examples include, but are not limited to, flow cytometry, Cel I assay, and the like.

Kits

Another aspect of the instant invention involves kits for transducing T-cells and/or for expressing exogenous genes in T-cells. Such kits can be constructed by packaging the appropriate materials, including one or more compositions of the instant invention, preferably with appropriate labels, in suitable containers. Kits can also include additional reagents and materials (for example, suitable buffers, salt solutions, etc.) helpful for carrying out the procedures and/or for measuring the degree of transduction and/or transgene expression. In some embodiment, the kits also include a suitable set of instructions pertaining to the transduction and/or transgene expression methods disclosed herein.

In some embodiments, the kit comprises a co-stimulatory agent and an adenovirus vector, e.g., and adenoviral expression vector. A "co-stimulatory agent" as used herein can refer to any compound, composition, aggregate, solution, etc. that can provide a co-stimulatory signal for activation of a T cell. Examples include, but are not limited to, beads coated with anti-CD3 antibodies, beads coated with anti-CD3 and anti-CD28 antibodies, and IL-15, in combinations as described herein.

The adenovirus vector of the kit can be one or more of any of the adenoviral vectors described herein. In preferred embodiments, the vector is an adenoviral expression vector pseudotyped to facilitate transduction of T cells. In a specific embodiment, the vector comprises an Ad5/F35 vector. In some embodiments, the vector also carries an exogenous gene for introduction and/or expression in T cells. In other embodiments, the vector is provided without the foreign insert, e.g., where the vector is provided with adenoviral sequences and instruction for inserting an exogenous gene of choice by the user.

Those of skill in the art will recognize various uses for the improved methods and compositions described herein. For example, methods of the instant invention can be used in ex vivo applications, where higher transduction efficiency (in terms of percent transduced) and/or higher transgene expression levels are desired. Such applications include, but are not limited to gene modification, characterization of gene function, and altering properties of T-cells.

Gene Modification

With respect to gene modification, enhanced delivery and/or expression of nucleases can lead to increased gene disruption, gene alteration, and/or targeted integration. For example, in such applications the exogenous genetic material can comprise a nuclease such as zinc finger nucleases (ZFN), discussed in more detail below, such as CCR5-ZFNs (8267 and 8196z) and the GR-ZFNs (9674 and 9666). Integration may occur via NHEJ and/or through homologous directed repair donor (HDR), events to introduce the exogenous gene into a region altering a targeted gene and/or randomly disrupting various genes. HDR events involve providing a donor molecule with sequence homologous to the ZFN target site that can be used as the template for the HDR machinery.

In some embodiments, the vector used for transduction comprises a zinc finger pair. A zinc finger pair refers to two binding domains of one or more zinc finger proteins. The term "zinc finger protein" or "ZFP" refers to a protein having DNA binding domains that are stabilized by zinc. The individual DNA binding domains are typically referred to as "fingers." A ZFP has least one finger, typically two fingers, three fingers, four fingers, five fingers or six fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$—His-$(X)_{3-5}$-His (where X is any amino acid) (SEQ ID NO:29). Studies have demonstrated that a single zinc finger of this class consists of an alpha helix containing the two invariant histidine residues co-ordinated with zinc along with the two cysteine residues of a single beta turn (see, e.g., Berg & Shi, Science 271: 1081-1085 (1996)). Non-canonical (i.e., non-C2H2) zinc finger proteins are also described, for example in U.S. Pat. Nos. 7,273,923 and 7,262,054 and U.S. Patent Publication Nos. 20060246588; 20060246567; and 20030108880.

Zinc finger binding domains can be engineered to bind to a predetermined nucleotide sequence. See, e.g., U.S. Application Publication No. 2007/0059795. In preferred embodiments, e.g., the zinc finger pair can be directed to CCR5. In more preferred embodiments, e.g., the vector carries both a zinc finger pair directed to CCR5 and a nuclease (a ZFN), whereby the nuclease can specifically cut the CCR5 gene, as elaborated below.

Alternatively, DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996)*J. Mol. Biol.* 263:163-180; Argast et al. (1998)*J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

Zinc Finger Nucleases

Described herein are zinc finger nucleases (ZFNs) that can be used for gene inactivation, for example inactivation of the CCR5 gene. ZFNs comprise a zinc finger protein (ZFP) domain and a nuclease (cleavage) domain. Exemplary disclosures of zinc finger nucleases, and methods for their synthesis and use, are provided in U.S. Patent Application Publication Nos. 2003/0232410; 2005/0026157; 2005/0064474; 2005/0208489; and 2006/0188987; and PCT Publications WO 2005/84190 and WO 2007/014275. Exemplary CCR-5-targeted ZFNs, and methods for their synthesis and use, are disclosed in International Patent Publication WO 2007/139982, also incorporated in entirety herein.

A. Zinc Finger Proteins

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261 and U.S. Patent Application Publication No. 2004/0197892, all of which are incorporated by reference herein in their entireties. Design methods are also disclosed in U.S. Pat. Nos. 6,013,453; 6,479,626; 6,746,838; 6,866,997; 6,903,185; 7,030,215 and 7,153,949; and WO 01/53480, the disclosures of which are incorporated by reference in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; 6,242,568; 6,790,941; as well as WO 98/37186; WO 98/53057; WO 00/27878; WO 01/88197 and GB 2,338,237; the disclosures of which are incorporated by reference in their entireties. Enhancement of binding specificity for zinc finger binding domains has been described, for example, in co-owned U.S. Pat. No. 6,794,136.

In certain embodiments, the zinc finger domain of the zinc finger nucleases described herein binds to a target sequence in a CCR-5 gene. Table 1 describes a number of zinc finger binding domains that have been engineered to bind to nucleotide sequences in the human CCR-5 gene. Each row describes a separate zinc finger DNA-binding domain. The DNA target sequence for each domain is shown in the first column (DNA target sites indicated in uppercase letters; non-contacted nucleotides indicated in lowercase), and the second through fifth columns show the amino acid sequence of the recognition region (amino acids −1 through +6, with respect to the start of the helix) of each of the zinc fingers (F1 through F4) in the protein. Also provided in the first column is an identification number for each protein.

TABLE 1

Zinc finger nucleases targeted to the human CCR-5 gene r162 designs

| Target sequence | F1 | F2 | F3 | F4 |
|---|---|---|---|---|
| GATGAGGATGAC (SEQ ID NO: 1) 7296 | DRSNLSR (SEQ ID NO: 2) | TSANLSR (SEQ ID NO: 3) | RSDNLAR (SEQ ID NO: 4) | TSANLSR (SEQ ID NO: 3) |
| GATGAGGATGAC (SEQ ID NO: 1) 8181 | DRSNLSR (SEQ ID NO: 2) | ISSNLNS (SEQ ID NO: 5) | RSDNLAR (SEQ ID NO: 4) | TSANLSR (SEQ ID NO: 3) |
| GATGAGGATGAC (SEQ ID NO: 1) 8182 | DRSNLSR (SEQ ID NO: 2) | VSSNLTS (SEQ ID NO: 6) | RSDNLAR (SEQ ID NO: 4) | TSANLSR (SEQ ID NO: 3) |
| GATGAGGATGAC (SEQ ID NO: 1) 8262 | DRSNLSR (SEQ ID NO: 2) | ISSNLNS (SEQ ID NO: 5) | RSDNLAR (SEQ ID NO: 4) | NRDNLSR (SEQ ID NO: 7) |
| GATGAGGATGAC (SEQ ID NO: 1) 8266 | DRSNLSR (SEQ ID NO: 2) | ISSNLNS (SEQ ID NO: 5) | RSDNLAR (SEQ ID NO: 4) | TSGNLTR (SEQ ID NO: 8) |
| GATGAGGATGAC (SEQ ID NO: 1) 8267 | DRSNLSR (SEQ ID NO: 2) | VSSNLTS (SEQ ID NO: 6) | RSDNLAR (SEQ ID NO: 4) | TSGNLTR (SEQ ID NO: 8) |
| GATGAGGATGAC (SEQ ID NO: 1) 87741 | DRSNLSR (SEQ ID NO: 2) | TSGNLTR (SEQ ID NO: 8) | RSDNLAR (SEQ ID NO: 4) | TSGNLTR (SEQ ID NO: 8) |
| 168 | | | | |
| AAACTGCAAAAG (SEQ ID NO: 9) 7745 | RSDNLSV (SEQ ID NO: 10) | QNANRIT (SEQ ID NO: 11) | RSDVLSE (SEQ ID NO: 12) | QRNHRTT (SEQ ID NO: 13) |
| AAACTGCAAAAG (SEQ ID NO: 9) 8165 | RSDNLSN (SEQ ID NO: 14) | QNANRIT (SEQ ID NO: 11) | RSDVLSE (SEQ ID NO: 12) | QRNHRTT (SEQ ID NO: 13) |
| AAACTGCAAAAG (SEQ ID NO: 9) 8191 | RSDNLSV (SEQ ID NO: 10) | QRVNLIV (SEQ ID NO: 15) | RSDVLSE (SEQ ID NO:12) | QRNHRTT (SEQ ID NO: 13) |
| AAACTGCAAAAG (SEQ ID NO: 9) 8196 | RSDNLGV (SEQ ID NO: 16) | QKINLQV (SEQ ID NO: 17) | RSDVLSE (SEQ ID NO: 12) | QRNHRTT (SEQ ID NO: 13) |
| AAACTGCAAAAG (SEQ ID NO: 9) 8196z | RSDNLSV (SEQ ID NO: 10) | QKINLQV (SEQ ID NO: 17) | RSDVLSE (SEQ ID NO: 12) | QRNHRTT (SEQ ID NO: 13) |
| AAACTGCAAAAG (SEQ ID NO: 9) 8196zg | RSDNLGV (SEQ ID NO: 16) | QKINLQV (SEQ ID NO: 17) | RSDVLSE (SEQ ID NO: 12) | QRNHRTT (SEQ ID NO: 13) |

TABLE 1-continued

Zinc finger nucleases targeted to the human CCR-5 gene r162 designs

| Target sequence | F1 | F2 | F3 | F4 |
|---|---|---|---|---|
| AAACTGCAAAAG (SEQ ID NO: 9) 7568 | RSDHLSE (SEQ ID NO: 18) | QNANRIT (SEQ ID NO: 11) | RSDVLSE (SEQ ID NO: 12) | QRNHRTT (SEQ ID NO: 13) |
| r627 | | | | |
| GACAAGCAGCGG (SEQ ID NO: 19) 7524 | RSAHLSE (SEQ ID NO: 20) | RSANLSE (SEQ ID NO: 21) | RSANLSV (SEQ ID NO: 22) | DRANLSR (SEQ ID NO: 23 |
| 633 designs | | | | |
| CATCTGcTACTCG (SEQ ID NO: 24) 8040 | RSDSLSK (SEQ ID NO: 25) | DNSNRIK (SEQ ID NO: 26) | RSAVLSE (SEQ ID NO: 27) | TNSNRIT (SEQ ID NO: 28) |

In certain embodiments, a zinc finger binding domain as shown in Table I is fused to a cleavage half-domain, such as, for example, the cleavage domain of a Type IIs restriction endonuclease such as Fok1. A pair of such zinc finger/nuclease half-domain fusions are used for targeted cleavage, as disclosed, for example, in U.S. Patent Application Publication No. 2005/0064474. For example, ZFN-215 denotes the pair of fusion proteins containing the zinc finger binding domains designated 8267 (which recognizes the target sequence shown in SEQ ID NO:1 and comprises the 4 recognition helices depicted in SEQ ID NOs:2, 6, 4 and 8) and 8196z (which recognizes the target sequence shown in SEQ ID NO:9 and comprises the 4 recognition helices depicted in SEQ ID NOs:10, 17, 12 and 13). ZFN-201 denotes the pair of fusion proteins containing the zinc finger binding domains designated 8266 (which recognizes the target sequence shown in SEQ ID NO:1 and comprises the 4 recognition helices depicted in SEQ ID NOs: 2, 2, 4 and 8) and 8196z (which recognizes the target sequence shown in SEQ ID NO:9 and comprises the 4 recognition helices depicted in SEQ ID NOs:10, 17, 12 and 13).

For targeted cleavage, the near edges of the binding sites can separated by 5 or more nucleotide pairs, and each of the fusion proteins can bind to an opposite strand of the DNA target. Hence, any one of the proteins identified as an "r162 design" in Table 1 (indicating that it binds to the reverse strand and that the downstream edge of its binding site is at nucleotide 162) can be paired with any of the proteins identified as a "168 design" (indicating that it binds to the strand opposite that bound by the r162 designs and that the upstream edge of its binding site is at nucleotide 168). For example, protein 8267 can be paired with protein 8196 or with protein 8196z or with any of the other 168 designs; and protein 8266 can be paired with either of proteins 8196 or 8196z or with any other of the 168 designs. All pairwise combinations of the r162 and 168 designs can be used for targeted cleavage and mutagenesis of a CCR-5 gene. Similarly, the 7524 protein (or any other r627 design) can be used in conjunction with the 8040 protein (or any other 633 design) to obtain targeted cleavage and mutagenesis of a CCR-5 gene.

The CCR5-ZFNs described herein can be targeted to any sequence in the CCR5 genome. For example, CCR5 genomic sequences (including allelic variants such as CCR5-A32) are well known in the art and individuals homozygous for the CCR5-432 (see, e.g., Liu et al. (1996) Cell 367377), are resistant to HIV-1 infection.

B. Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996)J. Mol. Biol. 263:163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS, enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:42754279; Li et al. (1993) Proc. Natl. Acad. Sci. USA 90:2764-2768; Kim et al. (1994a) Proc. Nat'l. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fok1 cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Application Publication No. 2005/0064474 and International Patent Publication WO 2007/014275, incorporated herein in their entireties. Additional restriction enzymes also contain separable binding and cleavage domains, and these are contemplated by the present disclosure. See, for example, Roberts et al. (2003) Nucleic Acids Res. 31:418-420.

To enhance cleavage specificity, cleavage domains may also be modified. In certain embodiments, variants of the cleavage half-domain are employed, which variants that minimize or prevent homodimerization of the cleavage half-domains. Non-limiting examples of such modified cleavage half-domains are described in detail in WO 2007/014275, incorporated by reference in its entirety herein. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. See, e.g., U.S. Patent Publication Nos. 20050064474 and 20060188987; International Patent Publication WO 07/139898; Miller et al. (2007) Nat. Biotechnol. 25(7):778-785.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. See FIGS. 2, 3 and 4 of International Patent Publication WO 2007/139982, incorporated herein by reference.

Figure 3A:
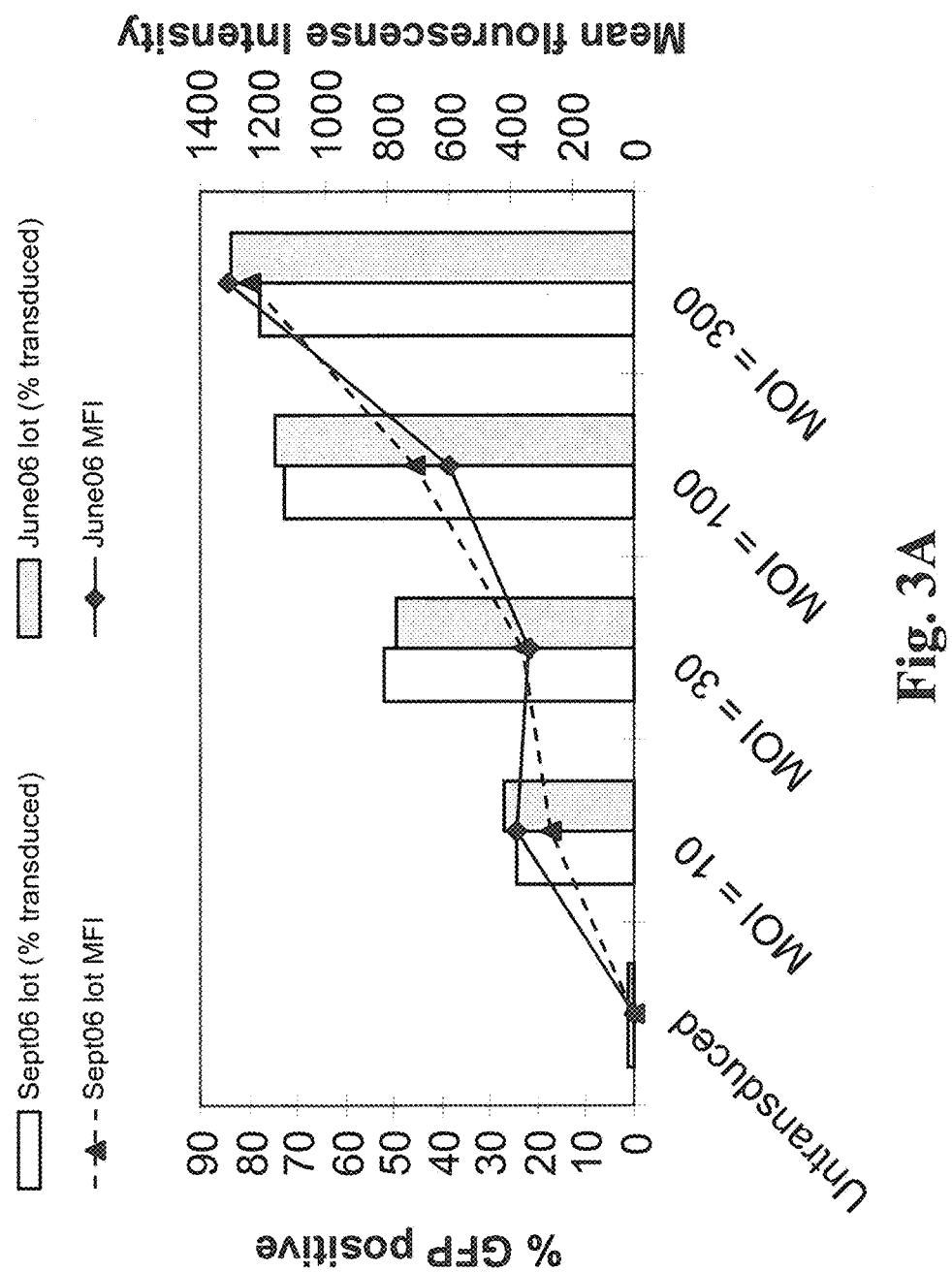
FIGS. 3A and 3B are graphs illustrating transduction and expression using 2 different lots of Ad5/F35 GFP adenoviral vectors, following activation with anti-CD3/anti-CD28 antibodies, in either primary T lymphocytes (FIG. 3A); or CD4+ cells (FIG. 3B).
Figure 3B:
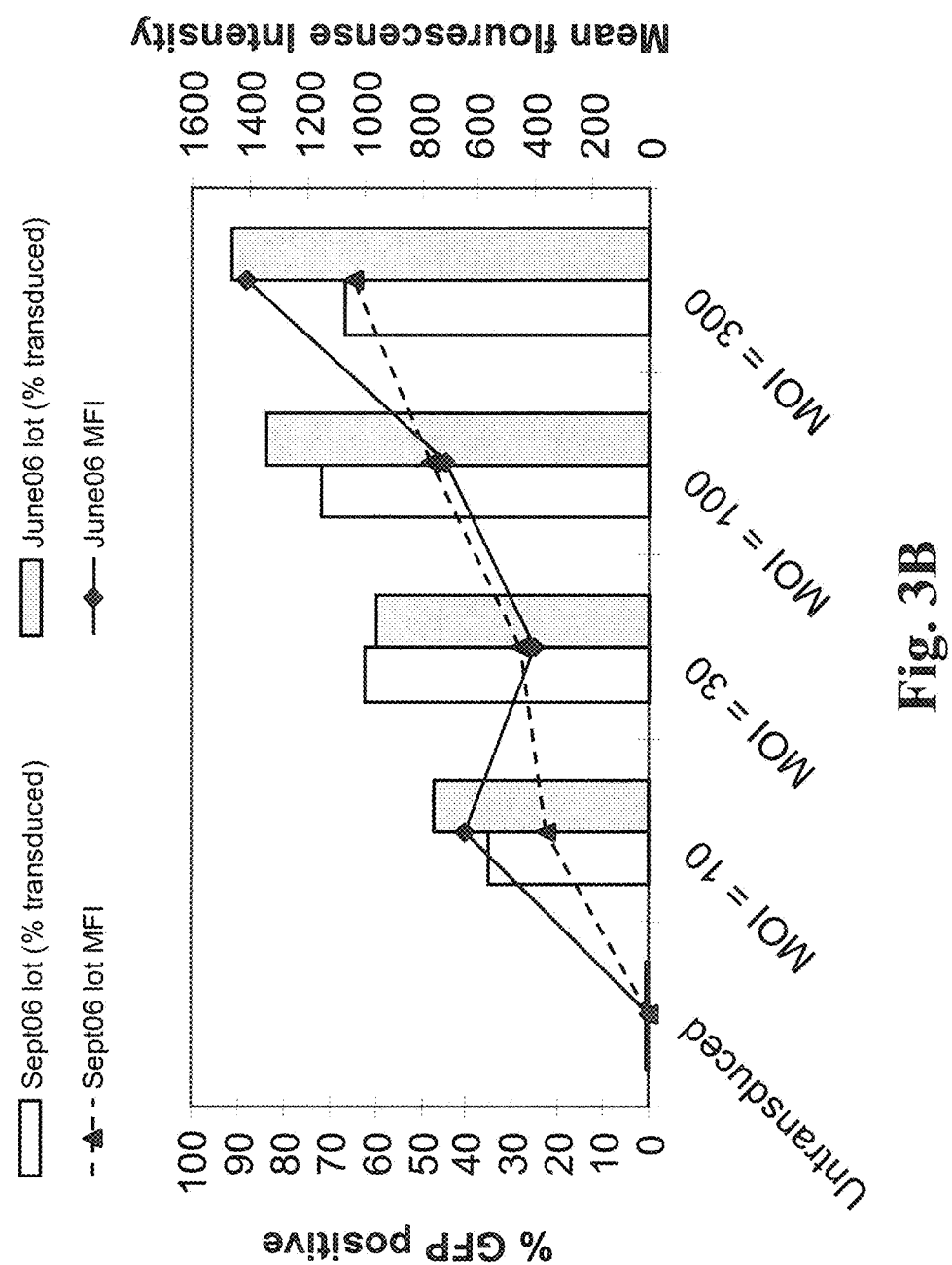
Figure 4:
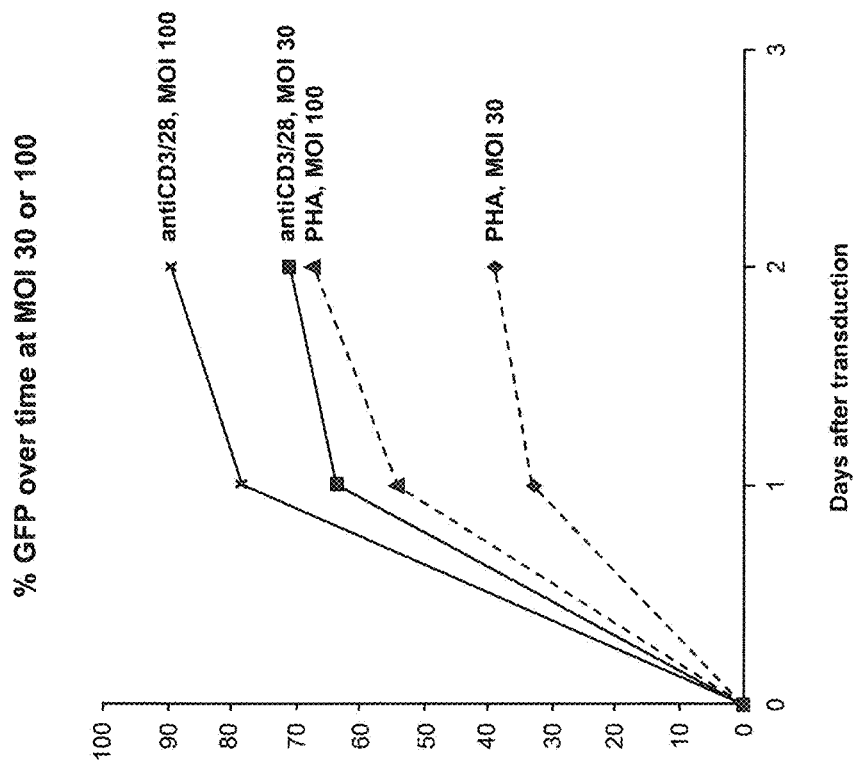
FIG. 4 is a graph illustrating transduction obtained in CD4+ cells over time, following activation with either PHA or anti-CD3/anti-CD28 antibodies at MOIs of 30 or 100.

Thus, in one embodiment, as shown in FIGS. 3 and 4, the mutation at 490 replaces Glu (E) with Lys (K); the mutation at 538 replaces Iso (I) with Lys (K); the mutation at 486 replaced Gin (Q) with Glu (E); and the mutation at position 499 replaces Iso (I) with Lys (K). Specifically, the engineered cleavage half-domains described herein were prepared by mutating positions 490 (E to K) and 538 (I to K) in one cleavage half-domain to produce an engineered cleavage half-domain designated "E490K:I538K" and by mutating positions 486 (Q to E) and 499 (I to L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of International Patent Publication No. 07/139898, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication No. 2005/0064474 (e.g., Example 5) and WO 2007/14275 (e.g., Example 38).

C. Additional Methods for Targeted Cleavage in CCR5

Any nuclease having a target site in a CCR5 gene can be used in the methods disclosed herein. For example, homing endonucleases and meganucleases have very long recognition sequences, some of which are likely to be present, on a statistical basis, once in a human-sized genome. Any such nuclease having a unique target site in a CCR5 gene can be used instead of, or in addition to, a zinc finger nuclease, for targeted cleavage in a CCR5 gene.

Exemplary homing endonucleases include I-SceI, I-CeuI, PI-PspI, PI-Sce, I-SceIV, I-CsmI, IPanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

Although the cleavage specificity of most homing endonucleases is not absolute with respect to their recognition sites, the sites are of sufficient length that a single cleavage event per mammalian sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66.

Gene Characterization

With respect to characterizing gene function, improved delivery and/or expression of cDNA cassettes can up-regulate to a greater extent expression of a gene being studied. As another example, improved delivery and/or expression of siRNA expression cassettes can down-regulate to a greater extent expression of a gene being studied. In either case, the enhanced change in expression can allow better characterization of gene function of T-cell genes.

Ex vivo applications also include altering the functional properties of a pool of transduced T cells. Examples of transgenes that can be used to alter T-cell function include, but are not limited to, chimeric T-cell receptors that can re-target a pool of T-cells against a specific antigen; and cytokines that can be over-expressed to enhance immune function and/or anti-viral activity, as provided in more detail below.

Treatments

The methods and compositions described herein can also find use in the treatment of a number of hematological, immunological and/or genetic conditions in animal subjects. The term "treating" (and its grammatical variants) as used herein includes achieving a therapeutic benefit and/or a prophylactic benefit. By therapeutic benefit is meant eradication or amelioration of the underlying condition being treated. Also, a therapeutic benefit is achieved with the eradication or amelioration of one or more of the physiological symptoms associated with the underlying condition such that an improvement is observed in the subject, notwithstanding the fact that the subject may still be afflicted with the condition. For prophylactic benefit, a composition of the present invention may be administered to a subject at risk of developing a condition, or to a subject reporting one or more of the physiological symptoms of such a condition, even though a diagnosis may not have been made.

The invention also provides pharmaceutical compositions for administration to a subject that can be treated using one or more of the methods and/or compositions disclosed herein. In some embodiments, pharmaceutical compositions comprise a therapeutic gene as the exogenous gene carried by the adenoviral vector and introduced into host cells ex vivo. By "therapeutic gene" is meant a nucleic acid molecule that when transduced and/or expressed produces a beneficial result in a subject receiving treatment. Examples of such therapeutic genes include IL2, which enhances T-cell expansion and can find use in treatment of patients with cancer; as well as CD40L (gp39 or CD154), which plays a role in TIC cell interaction and APC maturation and can find use in treatment of patients with certain types of leukemia. As a specific example, it has been demonstrated that an allosterically controllable ribozyme induces cell death in chronic myelogenous leukemia (CML) cell line harboring the b2a2 type bcr-abl oncogene in vitro and in vivo. Tanabe et al., Nature 2000, 406: 473-474. Some embodiments of the instant invention can find use in transducing the ribozyme into primary T cells of patients with CML, e.g., where the ribozyme can be transduced and expressed at high levels using one or more approaches taught herein.

Immunological Disorders

In one embodiment, the therapeutic proteins expressed by the transduced T cells possess immunomodulatory activity. For example, a therapeutic polypeptide of the present invention may be useful in treating deficiencies or disorders of the immune system, by activating or inhibiting the proliferation, differentiation, or mobilization (chemotaxis) of immune cells. Immune cells develop through the process of hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g. by chemotherapy or toxins), or infectious.

A therapeutic polypeptide of the present invention may be useful in treating deficiencies or disorders of hematopoietic cells. A therapeutic polypeptide of the present invention could be used to increase differentiation or proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

A therapeutic polypeptide of the present invention may also be useful in treating autoimmune disorders. Many autoimmune disorders result from inappropriate recognition of self as foreign material by immune cells. This inappropriate recognition results in an immune response leading to the destruction of the host tissue. Therefore, the administration of a therapeutic polypeptide of the present invention that inhibits an immune response, particularly the proliferation, differentiation, or chemotaxis of T-cells, may be an effective therapy in preventing autoimmune disorders.

Examples of autoimmune disorders that can be treated by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff Man Syndrome, Autoimmune Thyroiditis, Systemic Lupus Erythematosus, Autoimmune Pulmonary Inflammation, Guillain-Barre Syndrome, insulin-dependent diabetes mellitus, Crohn's disease, ulcerative colitis, and autoimmune inflammatory eye disease.

Similarly, allergic reactions and conditions, such as asthma (particularly allergic asthma) or other respiratory problems, may also be treated by a therapeutic polypeptide of the present invention.

Moreover, these molecules can be used to treat anaphylaxis, hypersensitivity to an antigenic molecule, or blood group incompatibility.

A therapeutic polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a therapeutic polypeptide of the present invention that inhibits an immune response, particularly the proliferation, differentiation, or chemotaxis of T-cells, may be an effective therapy in preventing organ rejection or GVHD.

Similarly, a therapeutic polypeptide of the present invention may also be used to modulate inflammation. For example, the therapeutic polypeptide may inhibit the proliferation and differentiation of cells involved in an inflammatory response. These molecules can be used to treat inflammatory conditions, both chronic and acute conditions, including inflammation associated with infection (e.g. septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g. TNF or IL-1).

Examples of classes of proteins having immunomodulatory activity include cytokines and thymic hormones. Thymic hormones include, for example, prothymosin-.alpha., thymulin, thymic humoral factor (THF), THF-γ-2, thymocyte growth peptide (TGP), thymopoietin (TPO), thymopentin, and thymosin-α-1. The term cytokine refers to a diverse group of secreted, soluble proteins and peptides that mediate communication among cells and modulate the functional activities of individual cells and tissues. Classes of cytokines include interleukins, interferons, colony stimulating factors, and chemokines. Examples of cytokines include: IL-1α, IL-1β, IL-2 through IL-30, leukocyte inhibitory factor (LIF), IFN-α, IFN-.gamma., TNF, TNF-α, TGF-β, G-CSF, M-CSF, and GM-CSF. One or more cytokines can be introduced and over-expressed in T cells, e.g., to enhance immune function and/or anti-viral properties.

Hyperproliferative Disorders

In one embodiment, a therapeutic protein of the invention is capable of modulating cell proliferation. Such a therapeutic polypeptide can be used to treat hyperproliferative disorders, including neoplasms.

Examples of hyperproliferative disorders that can be treated by a therapeutic polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated by a therapeutic polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

A therapeutic polypeptide expressed by a transgene according to the present invention may inhibit the proliferation of the disorder through direct or indirect interactions. Systemic administration of the transduced cells provides for access of therapeutic protein to a wide variety of tissues. Alternatively, a therapeutic polypeptide of the present invention may stimulate the proliferation of other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as with a chemotherapeutic agent.

Infectious Disease

In one embodiment, a therapeutic polypeptide of the present invention can be used to treat infectious disease. For example, by increasing the immune response, particularly increasing the proliferation and differentiation of B and/or T cells, infectious diseases may be treated. The immune response may be increased by either enhancing an existing immune response, or by initiating a new immune response. Alternatively, the therapeutic polypeptide of the present invention may also directly inhibit the infectious agent, without necessarily eliciting an immune response.

Viruses are one example of an infectious agent that can cause disease or symptoms that can be treated by a therapeutic polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), HIV, Herpesviridae (such as, Cytomegalovirus, Herpes Simplex, Herpes Zoster), Mononegavirus (e.g. Paramyxoviridae, Morbillivirus, Rhabdoviridae), Orthomyxoviridae (e.g. Influenza), Papovaviridae, Parvoviridae, Picornaviridae, Poxviridae (such as Smallpox or Vaccinia), Reoviridae (e.g. Rotavirus), Retroviridae (HTLV-I, HTLV-II, Lentivirus), and Togaviridae (e.g. Rubivirus). Viruses falling within these families can cause a variety of diseases or symptoms, including, but not limited to: arthritis, bronchiollitis, encephalitis, eye infections (e.g. conjunctivitis, keratitis), chronic fatigue syndrome, hepatitis (A, B, C, E, Chronic Active, Delta), meningitis, opportunistic infections (e.g. AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g. Kaposi's, warts), and viremia. A therapeutic polypeptide of the present invention can be used to treat any of these symptoms or diseases.

With respect to HIV infection, one approach involves using adenoviral vectors carrying zinc finger nucleases targeted to regions of the CCR5 gene as the transgene, as described in more detail above. See also, e.g., International Patent Publication WO 2007/139982, also incorporated in entirety herein. According to some embodiments of the instant invention, improved transduction and transgene expression can be achieved, resulting in efficient targeting and cleavage within the CCR5.

Bacterial or fungal agents that can cause disease or symptoms and that can be treated or detected by a therapeutic polypeptide of the present invention include, but are not limited to, the following Gram-Negative and Gram-positive bacterial families and fungi: Actinomycetales (e.g. *Corynebacterium, Mycobacterium, Norcardia*), Aspergillosis, Bacillaceae (e.g. Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g. *Acinetobacter*, Gonorrhea, Menigococcal), Pasteurellacea Infections (e.g. *Actinobacillus*, Heamophilus, *Pasteurella*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g. AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g. cellulitis, dermatocycoses), toxemia, urinary tract infections, wound infections. A therapeutic polypeptide of the present invention can be used to treat any of these symptoms or diseases.

Moreover, parasitic agents causing disease or symptoms that can be treated by a therapeutic polypeptide of the present invention include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g. dysentery, giardiasis), liver disease, lung disease, opportunistic infections (e.g. AIDS related), Malaria, pregnancy complications, and toxoplasmosis. A therapeutic polypeptide of the present invention can be used to treat any of these symptoms or diseases.

Regeneration

A therapeutic polypeptide of the present invention can be used to differentiate, proliferate, and attract cells, fostering to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated with the contribution of a therapeutic protein of the invention include organs (e.g. pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration incurs a small amount of scarring, or occurs without scarring. Regeneration also may include angiogenesis.

Moreover, a therapeutic polypeptide of the present invention may increase regeneration of tissues difficult to heal. For example, increased tendon/ligament regeneration would quicken recovery time after damage. A therapeutic polypeptide of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Chemotaxis

In one embodiment, a therapeutic polypeptide of the present invention possesses a chemotaxis activity. A chemotaxic molecule attracts or mobilizes cells (e.g. monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A therapeutic polypeptide of the present invention may increase the chemotaxic activity of the transduced cells. The expressed chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting additional immune cells to the injured location. Chemotactic molecules of the present invention can also attract fibroblasts, which can be used to treat wounds.

It is also contemplated that a therapeutic polypeptide of the present invention may inhibit chemotactic activity. These molecules could also be used to treat disorders. Thus, a therapeutic polypeptide of the present invention could be used as an inhibitor of chemotaxis.

Additional therapeutic polypeptides contemplated for use include, but are not limited to, growth factors (e.g., growth hormone, insulin-like growth factor-1, platelet-derived growth factor, epidermal growth factor, acidic and basic fibroblast growth factors, transforming growth factor-(3, etc.), to treat growth disorders or wasting syndromes; and antibodies (e.g., human or humanized), to provide passive immunization or protection of a subject against foreign antigens or pathogens (e.g., H. *Pylori*), or to provide treatment of cancer, arthritis or cardiovascular disease; cytokines, interferons (e.g., interferon (INF), INF-a2b and 2a, INF-aN1, INF-(31b, INF-gamma), interleukins (e.g., IL-1 to IL 10), tumor necrosis factor (TNF-α TNF-R), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (WA), urokinase, streptokinase, phenylalanine ammonia lyase, brain-derived neurotrophic factor (BDNF), nerve growth factor (NGF), thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone (PTH)-like, hormone, soluble CD4, and antibodies and/or antigen-binding fragments (e.g, FAbs) thereof (e.g., orthoclone OKT-3 (anti-CD3), GPllb/lla monoclonal antibody).

Those of skill in the art will recognize other therapeutic gene products that can be expressed in transduced cells using methods and/or compositions of various embodiments of the instant invention. See, e.g., additional examples listed in US Application Publication No. 20070059833. One of skill in the art will also recognize the utility of methods disclosed herein to gene therapy. In gene therapy, genetic information is usually delivered to a host cell in order to correct (supplement) a genetic deficiency in the cell, to inhibit an undesired function in the cell, or to eliminate the host cell. The genetic information can also be intended to provide the host cell with a desired function, for instance, to supply a secreted protein to treat other cells of the host, etc.

In some embodiments, one of more therapeutic gene products may be purified for use in pharmaceutical preparations. In some embodiments, the transgenic T cells themselves may be used therapeutically, such that the pharmaceutical composition comprises transgenic T cells, as described in more detail below.

In some embodiments, a pharmaceutically acceptable carrier is included in the pharmaceutical composition. Pharmaceutically acceptable carriers are determined in part by the particular composition being administered, as well as by the particular method used to administer the composition. Accordingly, there is a wide variety of suitable formulations of pharmaceutical compositions available (see, e.g., Remington's Pharmaceutical Sciences, 17th ed., 1989).

A pharmaceutical composition of the instant invention can be administered to a subject in need thereof in an effective amount. The effective amount when referring to a pharmaceutical composition comprising T cells transduced as described herein, will generally mean the dose ranges, modes of administration, formulations, etc., that have been recommended or approved by any of the various regulatory or advisory organizations in the medical or pharmaceutical arts (e.g., FDA, AMA) or by the manufacturer or supplier. The effective amount when referring to producing a benefit in treating a given condition, such as leukemia, will generally mean the amount that achieves clinical results recommended or approved by any of the various regulatory or advisory organizations in the medical or surgical arts (e.g., FDA, AMA) or by the manufacturer or supplier.

A person of ordinary skill using techniques known in the art can determine the effective amount of the transduced T cell described herein to be administered. The effective amount may depend on the exogenous gene and/or co-stimulatory agent being used, and can be deduced from known data, e.g., data regarding desired expression of the exogenous gene, measures of the exogenous gene obtained ex vivo (for example, as provided in the Examples herein) and/or in animal models, along with knowledge of translation of such data to the subject to be treated.

The pharmaceutical compositions can be administered by various means known in the art. For example, vectors can be delivered to cells ex vivo, such as cells explanted from an individual patient (e.g., lymphocytes, bone marrow aspirates, tissue biopsy), followed by re-implantation of the cells into a patient, usually after selection for cells which have incorporated the vector. Therapies where cells are genetically modified ex vivo, and then re-introduced into a subject can be referred to as cell-based therapies or cell therapies. In a preferred embodiment, cells are isolated from the subject organism, transduced with an exogenous gene (gene or cDNA) according to the present disclosure, and re-infused back into the subject organism (e.g., a patient). As a specific example, autologous cancer cells can be modified according to some embodiments of the present invention to express one or more immunostimulatory proteins and then may be re-introduced into the patient, e.g., as a cancer vaccine.

One of skill in the art will recognize several advantages of embodiments of the instant invention arising from the unexpected high transduction and/or transgene expression efficiencies taught herein. In particular, the use of adenoviral vectors can produce certain advantages over lentiviral vectors. For example, adenovirus can be engineered to carry large payloads, such that the vector carries larger inserts of exogenous genetic material. For example, Ad5 vectors typically have a deletion in the early transcribed genes (E1 and/or E3) of the viral genome, where novel genetic information can be introduced (the E1 deletion also renders the recombinant virus replication defective). Furthermore, large quantities of vector can be generated to transduce large quantities of cells in a single round. As is known in the art, adenovirus vectors are relatively easy to concentrate and purify. Moreover, clinical studies have provided valuable information on the use of these vectors in patients.

In addition, the improved delivery and/or expression efficiencies require less adenovirus to achieve a given effect. Accordingly, cytotoxicity caused by excessive exposure to adenovirus (within the cells and/or in the culture media) can be reduced by practicing some embodiments of the instant invention. Additionally, where cells are transduced in a manner favoring long-term culture, the long-term effects of transduced cells, e.g., expressing the desired transgene for an extended period of time, can be analyzed. Some embodiments of the instant invention therefore better facilitate long-term cultures and/or studies thereof. Of particular interest is the fact that such conditions can allow for the clinical manufacture of transgenetic material after adenovirus transduction. For example, in some embodiments, more that $100^9$, more that $100^{11}$ or more that $100^{13}$ cells can be obtained by culturing after adenovirus transduction. Accordingly, the present invention can also be used to produce more efficiently transgenic cells for use in cell therapy.

One of skill in the art will recognize other applications in which enhanced introduction and/or expression of genetic information in T cells would be desirable, in light of the detailed disclosures provided herein.

All citations are expressly incorporated herein in their entirety by reference.

EXPERIMENTAL

Example 1: Transduction of Anti-CD3/Anti-CD28-Activated T-Lymphocytes

A. CD3Ab/CD28Ab-Activated T-Cells

Primary T lymphocytes were obtained from healthy donors. In the case of frozen samples, the cells were thawed and cultured in RPMI medium supplemented with 10% FBS 1% L-glutamine and 10 ng/mL IL-2 (Sigma 12644) at a cell density of 1 E6 cells/mL. T lymphocytes were immediately activated via the anti-CD3/anti-CD28 pathway with Dynalbead CD3/CD28 (Invitrogen, Carlsbad, Calif.). Preparation and usage of the Dynalbead were performed according to the manufacturer's protocol. Briefly, resuspended beads (75 uL of resuspended Dynalbead per 1 E6 cells/mL) were washed three times with media in an eppendorf tube. Pelleting of beads in between washes was performed with a magnet. T lymphocyte cultures were incubated at 37° C., 5% $CO_2$ for 15 to 48 hours.

Following incubation, activated T lymphocytes were diluted to 3E5 to 1 E6 cells/mL. Ad5/F35 vectors were diluted with culture medium to transduce T lymphocytes at a multiplicity of infection (MOI) in the range of 10 to 1000 infectious units per cell. Diluted Ad5/F35 vectors were then added directly to the T lymphocytes and returned to the incubator. Gene delivery efficiencies were assessed by flow cytometry (when Ad5/F35 GFP vector was used) or the Cel I assay (when Ad5/F35 ZFN vectors were used).

As shown in FIG. 1, up to 92 and 87% of activated T-cells were transduced with Ad5 or Ad5/35 vectors at MOIs 100 and 1000 IU/cell, with a mean fluorescent intensity (MFI) of 630 and 1780 respectively.

B. Comparison of Transduction Efficiency of Bead-Activated and IL-7 Activated T Cells Transduction efficiencies of adenoviral vectors into IL-7-stimulated T lymphocytes was also assessed. Briefly, primary T cell were obtained and activated as described in Example 1, except that 10 ng/mL of IL-7 in the T cell culture was used for activation instead of Dynalbead CD3/CD28.

Figure 2A:
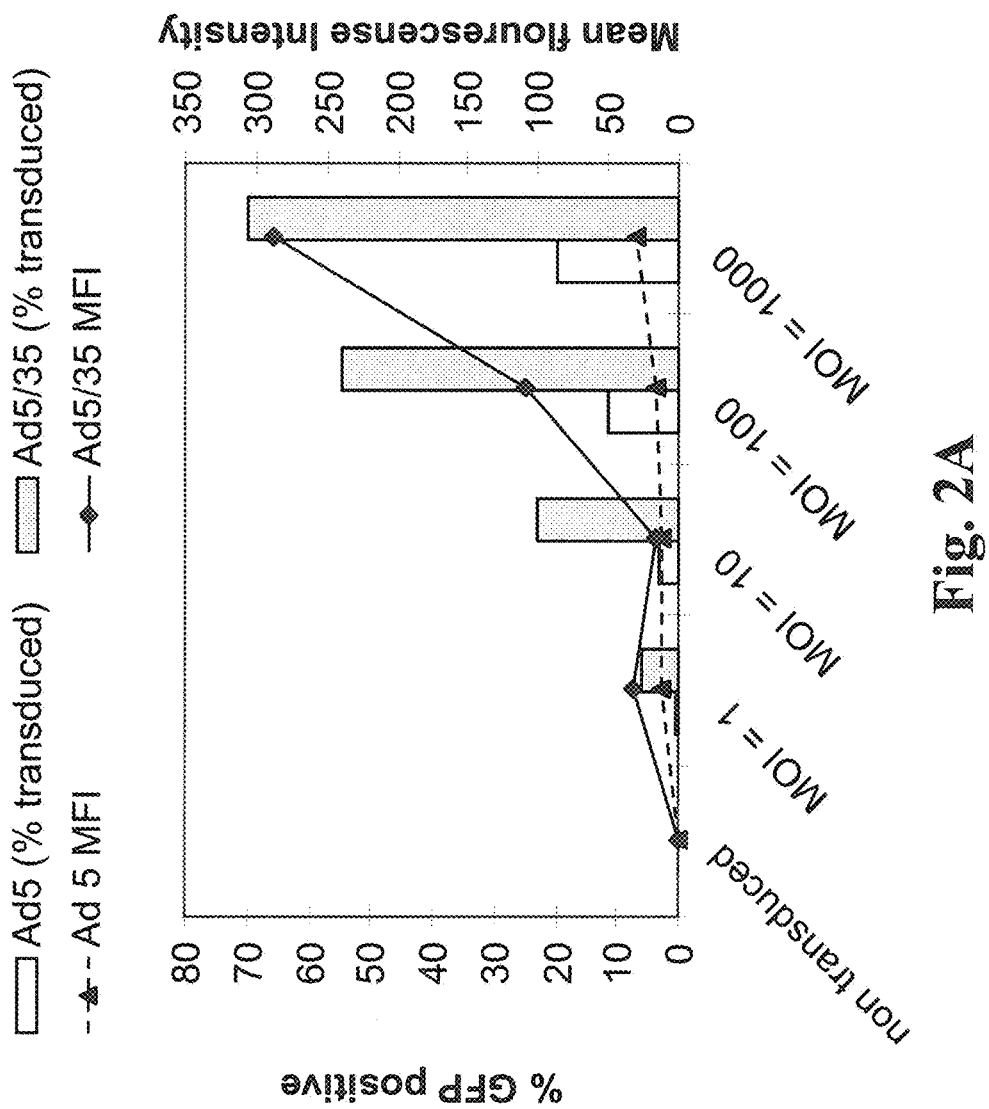
FIGS. 2A and 2B are graphs illustrating transduction and expression levels of GFP in CD4+ cells using either Ad5 or Ad5/F35 GFP adenoviral vectors, following activation with IL-7 (FIG. 2A); or (B) anti-CD3/anti-CD28 antibodies (FIG. 2B).
Figure 2B:
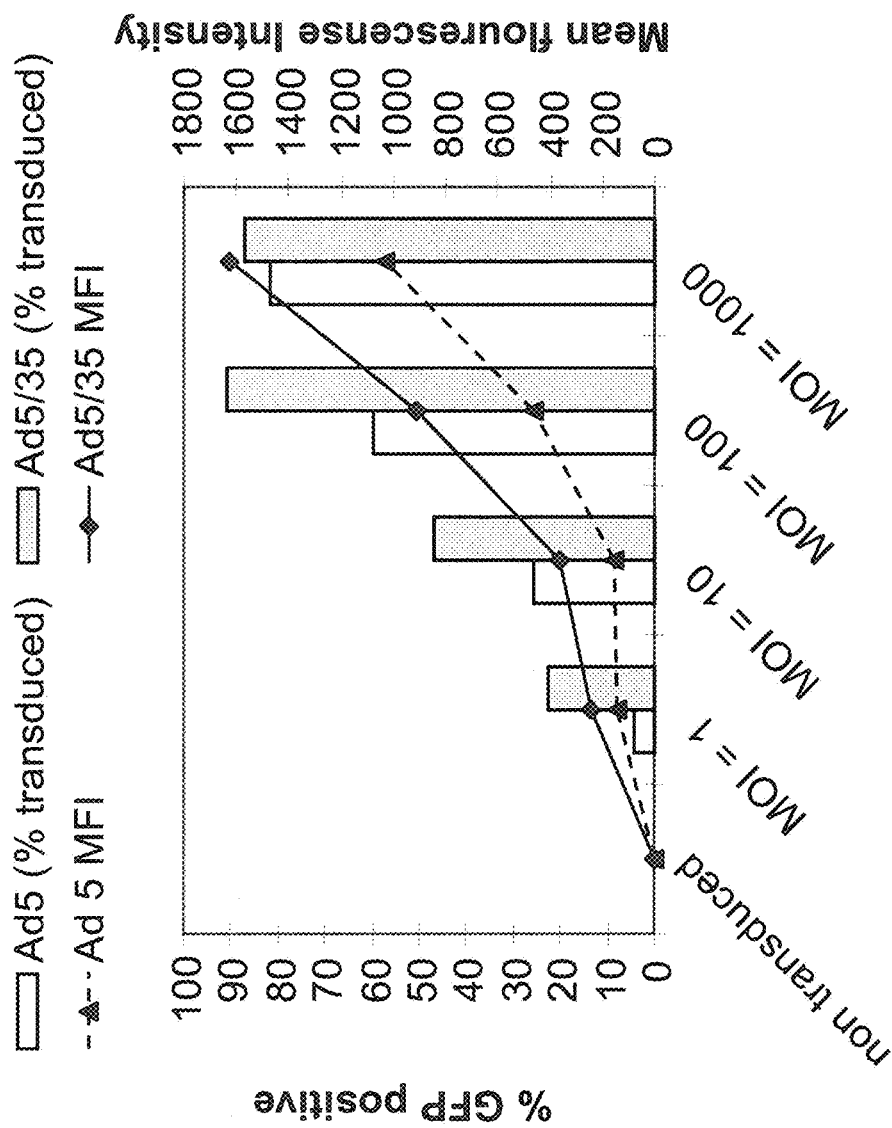

As shown in FIGS. 2A and B, at MOIs of 100 and 1000 IU/cell, T cells activated by IL-7 yielded a transduction percentage of 55% and 70%, with MFIs of 109 and 288. By comparison, T cells activated by Dynalbeads were transduced at 91% and 87%, with MFIs of 910 and 1620, respectively.

C. Comparison of Transduction Efficiency of Bead-Activated and PHA/IL2-Activated T Cells CD4+ T cells were also activated by the addition of PHA and IL2 or by addition of anti-CD3/anti-CD28 coated beads for 4 days. Following activation, the cells were transduced with the Ad5/35 GFP vector at an MOI of 30 or 100. The transduction efficiency comparing the two activation conditions at either MOI 30 or 100 was determined by FACS analysis measuring the percentage of cells expressing GFP within the first 2 days after transduction.

As shown in FIG. 4, bead-activated T-cells were transduced with higher efficiency than PHA/IL2 activated cells (example, at MOI of 30, approximately 35% of cells stimulated by PHA expressed GFP while 65% of those cells stimulated by anti CD3/28 expressed GFP).

These results demonstrate that Ad5/F35 transduction pre-stimulating T lymphocytes with beads that are coated with monoclonal antibodies against the CD3 and CD28 cell-surface receptors results in 60-90% transduction efficiencies, as compared to ~45% transduction efficiency of PHA-activated T lymphocytes. See, e.g., Schroers et al., supra. In addition, when directly compared with other methods of T lymphocyte stimulation (PHA or IL-7), T cells co-stimulated by anti-CD3/anti-CD28 bead activation achieved a significantly higher level of non-homologous end joining (NHEJ) events when transduced with an Ad5/F35 vector encoding for a pair of ZFNs targeting CCR5.

Example 2: Transduction of Anti-CD3/Anti-CD28 Bead-Activated T-Lymphocytes

Peripheral blood mononuclear cells (PBMC) and CD4 T-cells were also transduced with two different preparations (lots) of Ad5/35 GFP vector as described in Examples 1 and 2.

As shown in FIGS. 3A and 3B, at MOIs of 100 and 300, with either preparation, Ad5/35 GFP transduced PBMC and CD4 T cells at a high percentage (67-91%) and MFIs (598-1408). Similar transduction efficiencies were observed with both lots of Ad5/35 GFP vector.

Example 3: Transgene Expression

The levels of transgene expression in bead-activated T cells was also assessed. CD4 T cells were either activated by the addition of PHA and IL2 or by addition of anti-CD3/anti-CD28 coated beads for 4 days, and the cells were transduced with the Ad5/35 GFP vector at an MOI of 10, 30, or 100.

Figure 5A:
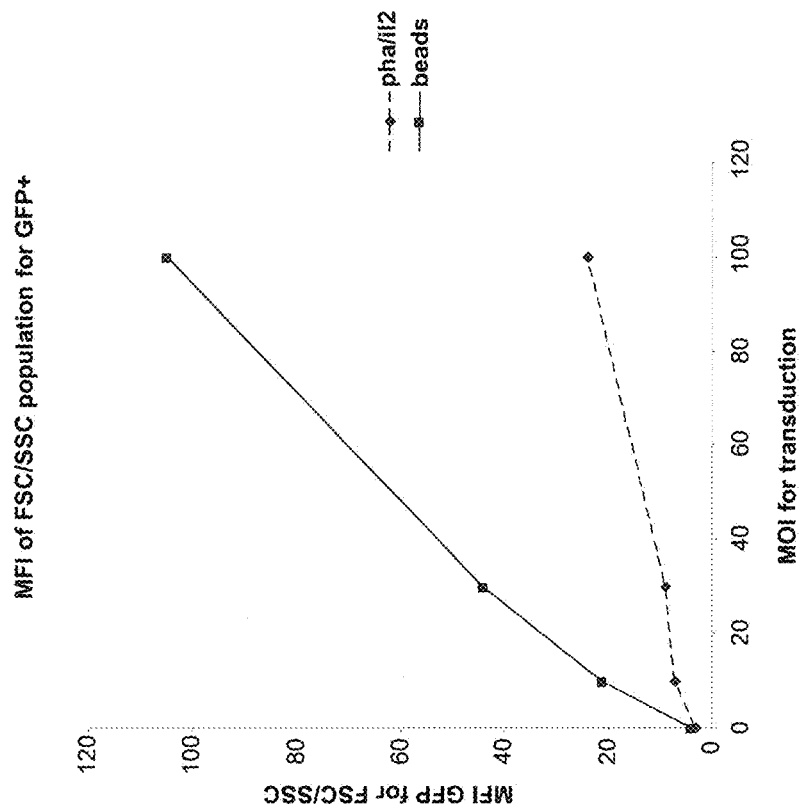
FIGS. 5A and 5B are graphs depicting transduction (FIG. 5A) and expression (FIG. 5B) of GFP Day 1 after transduction in CD4+ cells using Ad5/F35 GFP adenoviral vectors, following activation with either PHA/IL 2 or antiCD3/anti-CD28 antibodies.
Figure 5B:
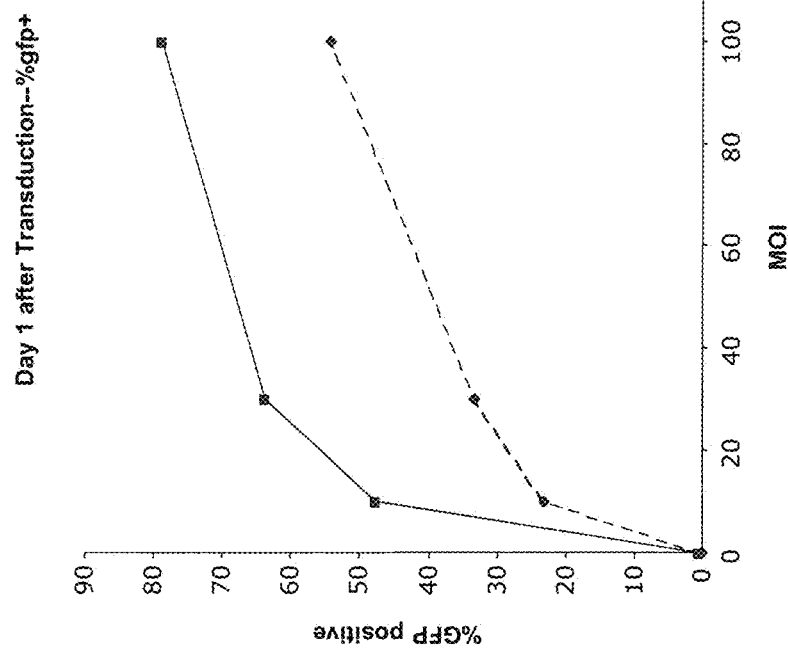
Figure 6A:
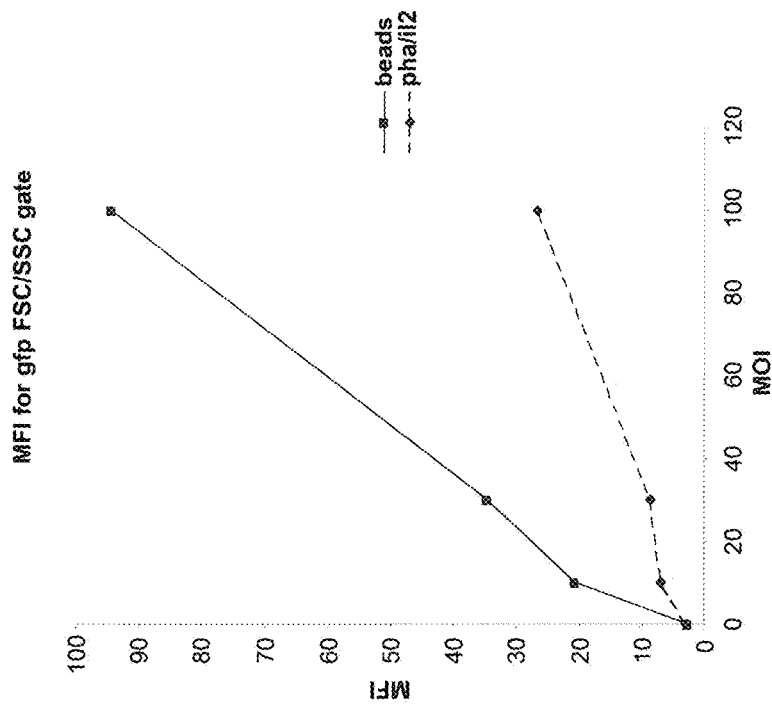
FIGS. 6A and 6B are graphs depicting transduction (FIG. 6A) and expression (FIG. 6B) of GFP Day 2 after transduction in CD4+ cells using Ad51F35 GFP adenoviral vectors, following activation with either PHA/IL 2 or antiCD3/anti-CD28 antibodies.
Figure 6B:
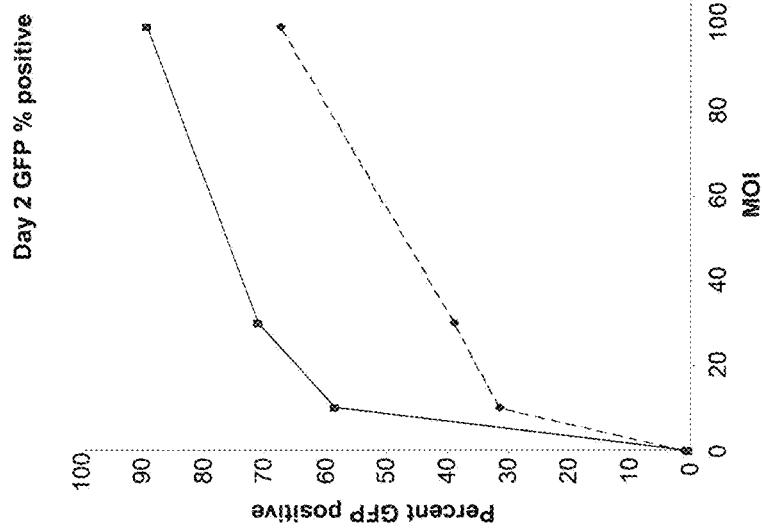

Transduction efficiency was determined by measuring the percentage of cells expressing GFP (FIGS. 5A and 6A) and the level of transgene expression was determined by measuring the mean fluorescence intensity of the transduced population (FIGS. 5B and 6B) for all 3 MOI conditions tested at day 1 (FIG. 5) and day 2 (FIG. 6) post-transduction.

Figure 7:
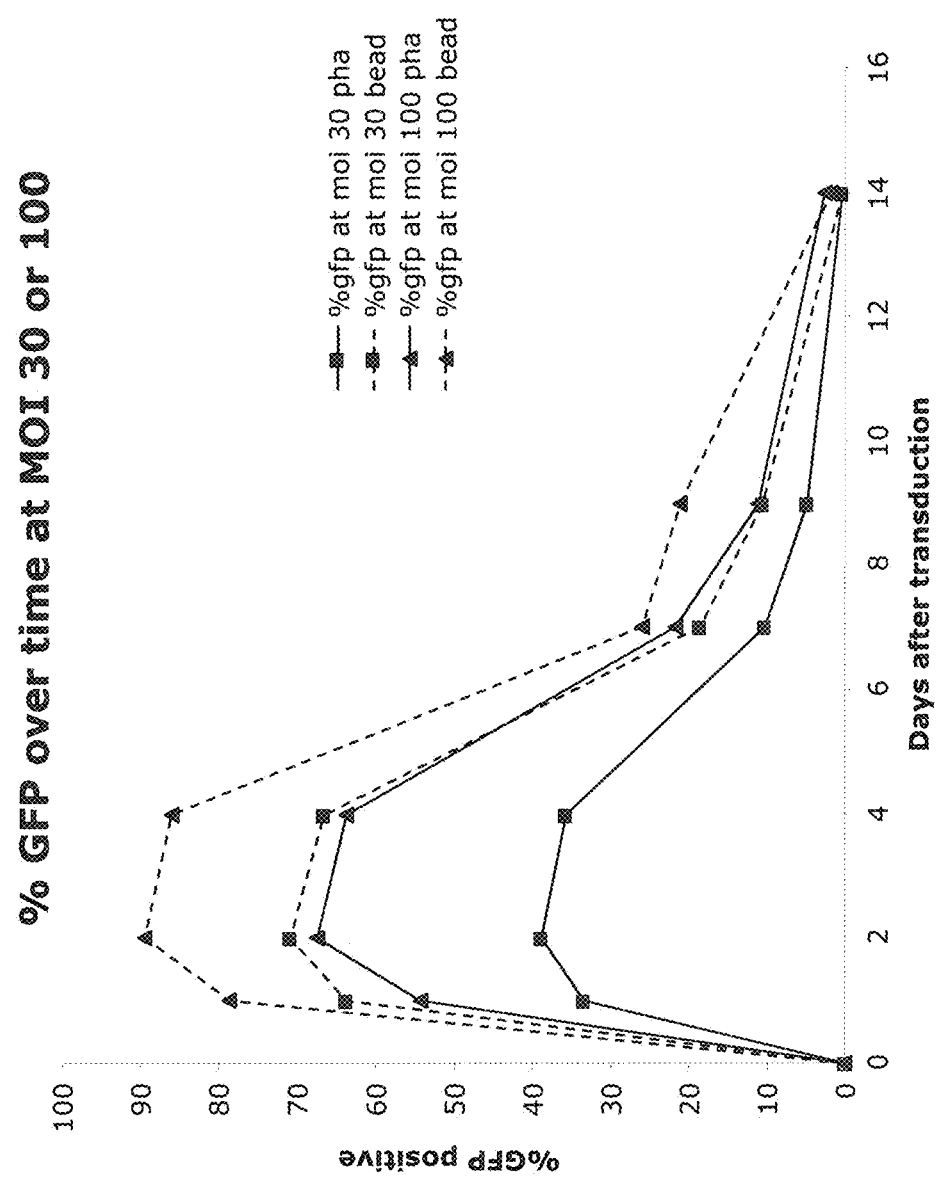
FIG. 7 is a graph depicting GFP expression obtained in CD4+ cells over time, following activation with either PHA or anti-CD3/anti-CD28 antibodies each the indicated MOIs of either 30 or 100.

To demonstrate that transgene expression was transient or that transgene expression was not affected by some delayed response created by the PHA/11-2 activation, GFP expression was monitored in the MOI 30 and 100 samples for an extended period of time out to day 14 post transduction. FIG. 7 shows the percentage of GFP-positive cells of bead-activated T cells transduced at MOI 30 (gray squares) or MOI 100 (gray triangles) as compared to PH-activated T cells transduced at MOI 30 (black squares) or MOI 100 (black triangles).

To also exclude the possibility that transgene expression was affected by a reduction in cell division and dilution of the transduced vector sequence, the rate of T cell expansion was also monitored by measuring the population doubling rate.

Figure 8:
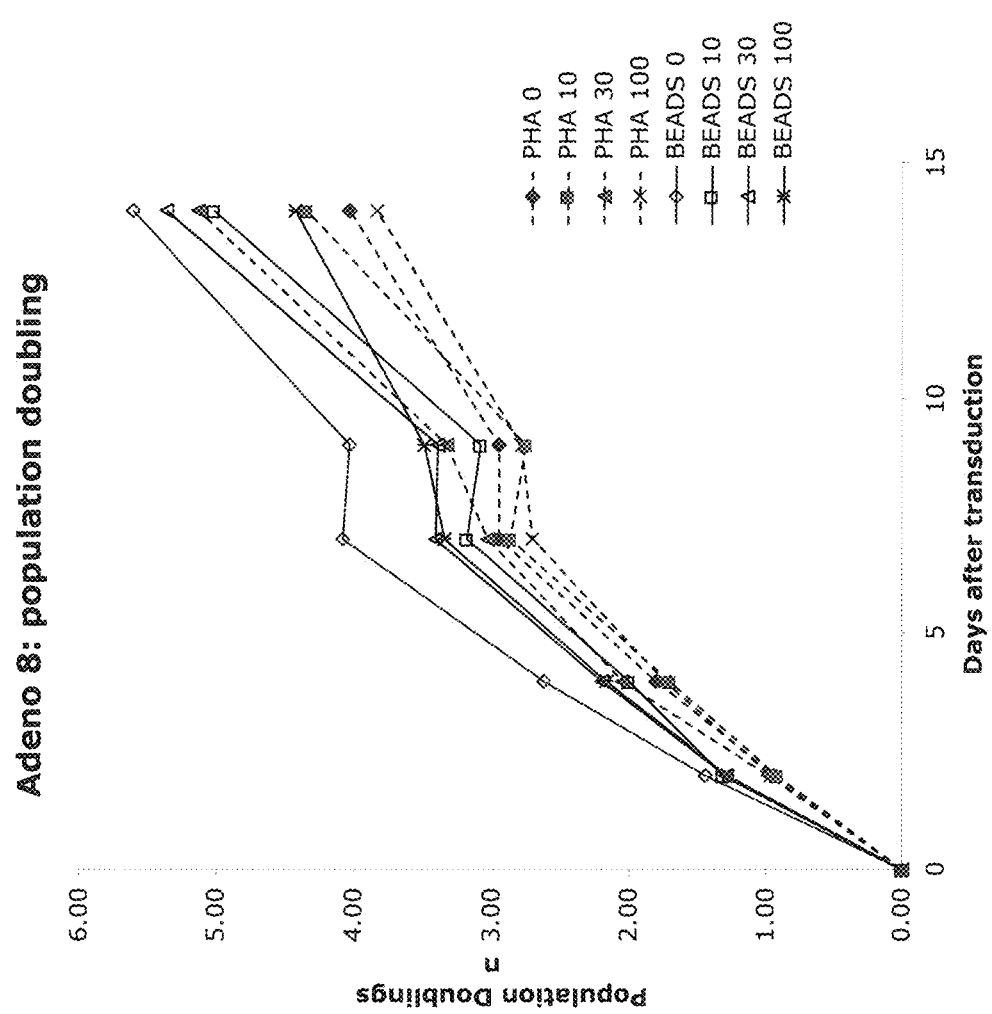
FIG. 8 illustrates T-cell expansion over time, following activation with either PHA or antiCD3/anti-CD28 antibodies each at MOIs of 0, 10, 30 or 100.
Figures 9A, 9B:
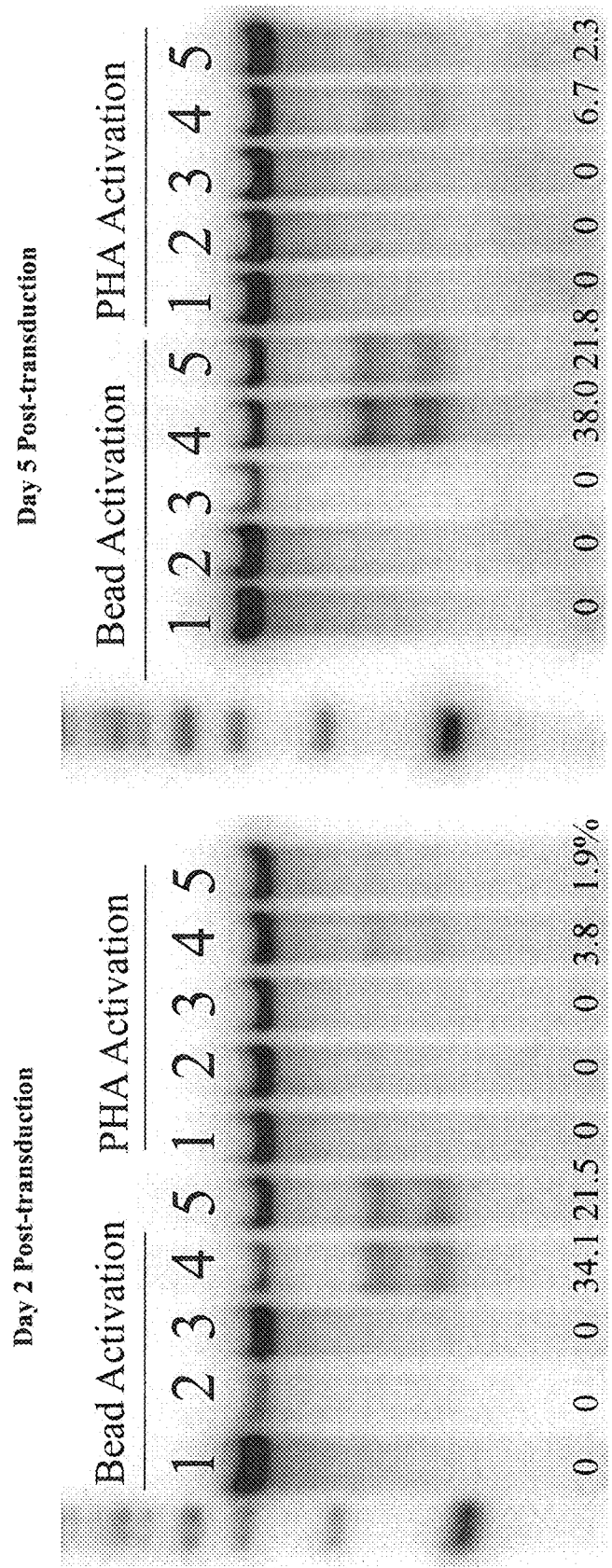
FIGS. 9A and 9B show gels depicting differences in CCR5 gene modification in CD4+ T cells exposed to Ad5/F35 vectors carrying a zinc finger nuclease directed to CCR5 when pre-stimulated with either PHA or anti-CD3/anti-CD28 antibodies. Lane 1 shows non-transduced cells; lane 2 shows cells transduced with an Ad5/F35 encoding GFP, lane 3 shows cells transduced with ZFNs targeting the IL2Rγ gene, lane 4 shows cells transduced with ZFNs targeting CCR5, and lane 5 shows cells transduced with a second set of CCR5 ZFNs. CCR5 and IL2Rγ-targeted ZFNs are described, for example, in International Patent Publication Nos. WO 2007/139982; 2005/014791 and WO 2005/084190. At the indicted days post-transduction, an aliquot of cells were harvested and genomic DNA harvested using the MasterPure™ DNA Purification Kit (Epicentre Biotechnologies). The level of ZFN activity in response to different activation conditions was assessed by measuring the efficiency of gene modification at the endogenous CCR5 locus using the Surveyor assay. The percentage of NHEJ events is shown beneath each lane.

As shown in FIG. 8, bead-activated T cells grew as well as or more robustly than PHA-activated T-cells. In addition, bead-activated T cells were transduced with adenovirus vectors at higher efficiencies than PHA-activated T cells. See, FIG. 9.

Example 4: Cleavage of Endogenous Targets

T-cells are activated with PHA/IL2 or anti-CD3/CD28 beads and transduced with the Ad5/F35 virus encoding GFP, the CCR5-ZFNs, and the GR-ZFNs as described above. Cells are harvested at day 3 and day 10 post-transduction and genomic DNA isolated. The ability of the ZFNs to cleave their respective target sites at CCR5 or GR is analyzed by Cell assays.

To examine how many viral copies have entered the cells, the number of viral genomes that are present per activated transduced cell is determined using a quantitative PCR assay that measures the number of Ad E4 genes per endogenous RNAP genes. Quantitative PCR is performed to determine whether the activation conditions effect transgene expression or affect the transduction efficiency (e.g., allowing more adenovirus particles to enter the cells).

After transduction with the GFP vector, flow cytometry is performed to measure the number (percentage) of cells transduced. The mean fluorescence intensity is also be determined to evaluate whether anti-CD3/CD28 bead results in transduction or more cells and/or increased levels of transgene expression (e.g., if the percentage of GFP positive cells remains relatively constant, but the mean fluorescence is increased). The difference in the level of Ad5/F35 receptor (CD46) on the cell surface in response to different activation conditions is also determined by flow cytometry. To determine whether transduction is in response to upregulation of CD46 receptors on the cell surface by anti-CD3/CD28 activation, the cells are stained using an anti-CD46 antibody and changes in the MFI are evaluated using flow cytometry.

Example 5: Transduction with Ad5/11

To demonstrate the versatility of the method, T-cells are prepared and activated as described in Example 1. The cells are then transduced with an Ad5/11 vector instead of Ad5/F35. Similar analysis is performed to verify T-cell transduction efficiency and transgene activity.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

All publications, articles, patents, and patent applications mentioned in this specification are herein incorporated by reference to the same extent as if each individual publication, article, patent or patent application was specifically and individually indicated as being incorporated by reference.

What is claimed is:

1. A method for expressing an exogenous sequence in CD4+ T-cells said method comprising:
   - activating a population of the CD4+ T-cells with anti-CD3/anti-CD28 beads;
   - contacting the CD+4 T-cells with a feeder cell: and
   - contacting the activated CD4+ T cell population with the feeder cells with one or more adenoviral expression vectors comprising said exogenous sequence and a sequence encoding a zinc finger nuclease, wherein the one or more expression vectors comprise control sequences that drive expression of the exogenous sequence and the zinc finger nuclease;
   - wherein T cells within the activated T cell population comprising the adenovirus vectors express the exogenous sequence.

2. The method according to claim 1, wherein the one or more adenoviral expression vectors are pseudotyped.

3. The method according to claim 2, wherein the one or more pseudotyped adenovirus expression vector comprises sequences from Ad5 and Ad35 adenoviruses.

4. The method according to claim 3, wherein the Ad35 sequence is F35.

5. The method according to claim 1, wherein the zinc finger nuclease binds to a target site in a CCR5 gene.

6. The method of claim 1, wherein the zinc finger nuclease cleaves an endogenous gene.

7. The method of claim 6, wherein the endogenous gene is a CCR5 gene.

* * * * *

SEQUENCE LISTING

<160> NUMBER OF SEQ ID NOS: 29

<210> SEQ ID NO 1
<211> LENGTH: 12
<212> TYPE: DNA
<213> ORGANISM: Artificial Sequence
<220> FEATURE:
<223> OTHER INFORMATION: Derived from human CCR-5 gene

<400> SEQUENCE: 1
gatgaggatg ac                                                                12

<210> SEQ ID NO 2
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 2

Asp Arg Ser Asn Leu Ser Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 3

Thr Ser Ala Asn Leu Ser Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 4

Arg Ser Asp Asn Leu Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 5

Ile Ser Ser Asn Leu Asn Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

```
<400> SEQUENCE: 6

Val Ser Ser Asn Leu Thr Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 7

Asn Arg Asp Asn Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 8

Thr Ser Gly Asn Leu Thr Arg
1               5

<210> SEQ ID NO 9
<211> LENGTH: 12
<212> TYPE: DNA
<213> ORGANISM: Artificial Sequence
<220> FEATURE:
<223> OTHER INFORMATION: Derived from human CCR-5 gene

<400> SEQUENCE: 9
aaactgcaaa ag                                                         12

<210> SEQ ID NO 10
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 10

Arg Ser Asp Asn Leu Ser Val
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 11

Gln Asn Ala Asn Arg Ile Thr
1               5

<210> SEQ ID NO 12
<211> LENGTH: 7
<212> TYPE: PRT
<213> ORGANISM: Artificial Sequence
<220> FEATURE:
```

<223> OTHER INFORMATION: Synthetic zinc finger DNA-binding domain
      targeted to human CCR-5 gene

<400> SEQUENCE: 12

Arg Ser Asp Val Leu Ser Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 13

Gln Arg Asn His Arg Thr Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 14

Arg Ser Asp Asn Leu Ser Asn
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 15

Gln Arg Val Asn Leu Ile Val
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 16

Arg Ser Asp Asn Leu Gly Val
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 17

Gln Lys Ile Asn Leu Gln Val
1               5

```
<210> SEQ ID NO 18
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 18

Arg Ser Asp His Leu Ser Glu
1               5

<210> SEQ ID NO 19
<211> LENGTH: 12
<212> TYPE: DNA
<213> ORGANISM: Artificial Sequence
<220> FEATURE:
<223> OTHER INFORMATION: Derived from human CCR-5 gene

<400> SEQUENCE: 19
gacaagcagc gg                                                        12

<210> SEQ ID NO 20
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 20

Arg Ser Ala His Leu Ser Glu
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 21

Arg Ser Ala Asn Leu Ser Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 22

Arg Ser Ala Asn Leu Ser Val
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 23

Asp Arg Ala Asn Leu Ser Arg
```

<210> SEQ ID NO 24
<211> LENGTH: 13
<212> TYPE: DNA
<213> ORGANISM: Artificial Sequence
<220> FEATURE:
<223> OTHER INFORMATION: Derived from human CCR-5 gene

<400> SEQUENCE: 24
catctgctac tcg                                                         13

<210> SEQ ID NO 25
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 25

Arg Ser Asp Ser Leu Ser Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 26

Asp Asn Ser Asn Arg Ile Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 27

Arg Ser Ala Val Leu Ser Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic zinc finger DNA-binding domain
      targeted to human CCR-5 gene

<400> SEQUENCE: 28

Thr Asn Ser Asn Arg Ile Thr
1               5

<210> SEQ ID NO 29
<211> LENGTH: 25
<212> TYPE: PRT
<213> ORGANISM: Artificial Sequence
<220> FEATURE:
<223> OTHER INFORMATION: Synthetic C2H2 Class Zinc Finger
<220> FEATURE:
<221> NAME/KEY: misc_feature

```
<222> LOCATION: (2)..(5)
<223> OTHER INFORMATION: At least 2 and up to 4 amino acids can be
      present or absent; if present, Xaa can be any naturally occurring
      amino acid
<220> FEATURE:
<221> NAME/KEY: misc_feature
<222> LOCATION: (7)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: At least 3 and up to 5 amino acids can be
      present or absent; if present, Xaa can be any naturally occurring
      amino acid

<400> SEQUENCE: 29

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25
```